United States Patent
Ji et al.

(10) Patent No.: US 11,584,726 B2
(45) Date of Patent: Feb. 21, 2023

(54) AMINO ALCOHOL DERIVATIVE, PHARMACEUTICAL COMPOSITION AND APPLICATION THEREOF

(71) Applicant: Beijing Foreland Pharma Co., Ltd., Beijing (CN)

(72) Inventors: Qi Ji, Beijing (CN); Xingmin Zhang, Beijing (CN); Zhenjian Du, Beijing (CN); Longlong Gong, Beijing (CN); Lei Wang, Beijing (CN); Congmin Gao, Beijing (CN); Meijing Du, Beijing (CN)

(73) Assignee: BEIJING FORELAND PHARMA CO., LTD., Beijing (CN)

( * ) Notice: Subject to any disclaimer, the term of this patent is extended or adjusted under 35 U.S.C. 154(b) by 235 days.

(21) Appl. No.: 16/625,151

(22) PCT Filed: Jun. 21, 2018

(86) PCT No.: PCT/CN2018/092233
§ 371 (c)(1),
(2) Date: Dec. 20, 2019

(87) PCT Pub. No.: WO2019/001342
PCT Pub. Date: Jan. 3, 2019

(65) Prior Publication Data
US 2021/0347745 A1    Nov. 11, 2021

(30) Foreign Application Priority Data
Jun. 30, 2017    (CN) .......................... 201710554216.6

(51) Int. Cl.
*C07D 271/06*    (2006.01)
*A61K 45/06*    (2006.01)
*C07D 413/04*    (2006.01)

(52) U.S. Cl.
CPC ............ *C07D 271/06* (2013.01); *A61K 45/06* (2013.01); *C07D 413/04* (2013.01)

(58) Field of Classification Search
CPC .............................. C07D 271/06; C07D 413/04
See application file for complete search history.

(56) References Cited

U.S. PATENT DOCUMENTS

2015/0094337 A1    4/2015    Zhang et al.

FOREIGN PATENT DOCUMENTS

| CN | 101768086 A | 7/2010 |
| CN | 102250035 A | 11/2011 |
| CN | 102816128 A | 12/2012 |
| JP | H02-85247 A | 3/1990 |
| WO | 82/04042 A1 | 11/1982 |

OTHER PUBLICATIONS

Wu et al., "Synthesis and Biological Evaluation of Amino Alcohol Containing 1,3,4-Oxadiazole", Chemical Research in Chinese Universities, vol. 32, No. 5, pp. 760-767 (2016).*
Wu et al., "Synthesis and Biological Evaluation of Amino Alcohol Containing 1,3,4-Oxadiazole," Chemical Research in Chinese Universities, 32 (5): 760-767 (2016).
International Search Report issued in corresponding International Patent Application No. PCT/CN2018/092233 dated Sep. 30, 2018.
Hanwen Sun, Introduction to Modern Science and Technology, Sep. 30, 1999 (see English abstract).
Zhulai Li, Pharmaceutical Chemistry Experiment Guidance, Jan. 31, 2014 (see English abstract).
Extended European Search Report issued in corresponding European Patent Application No. 18822870.4 dated Feb. 25, 2021.

* cited by examiner

*Primary Examiner* — Kevin E Weddington
(74) *Attorney, Agent, or Firm* — Morgan, Lewis & Bockius LLP

(57) ABSTRACT

The present invention belongs to the field of medicine, and specifically discloses an amino alcohol derivative represented by Formula I, a pharmaceutically acceptable salt, solvate, polymorph or prodrug thereof. In addition, the present invention also discloses a pharmaceutical composition comprising the above substances, and a use of the substance in the preparation of a medicament for the prevention and treatment of an immune inflammatory disease, or a disease or condition associated with immunological competence such as multiple sclerosis, ALS, CIDP, systemic lupus erythematosus, rheumatoid arthritis, ulcerative colitis, psoriasis, polymyositis, etc.

11 Claims, No Drawings

AMINO ALCOHOL DERIVATIVE, PHARMACEUTICAL COMPOSITION AND APPLICATION THEREOF

TECHNICAL FIELD

The present application belongs to medical field, particularly relates to an amino alcohol derivative, a pharmaceutical composition and application thereof.

BACKGROUND

The immune system is a self-defensive structure mainly consisting of lymphatic organs (thymus glands, lymph nodes, spleen, tonsils), lymphatic tissues within other organs, lymphocytes throughout the body, antigen presenting cell, and the like. The immune system also includes other leucocytes in blood, and plasma cells and mast cells in connective tissues. The key components of the immune system are lymphocytes, which endue the immune system with the capability of recognition and memory. The lymphocytes travel throughout the body via blood and lymph, migrating from one lymphatic organ or tissue to another lymphatic organ or tissue, and connecting the lymphatic organs or tissues scattered throughout the body to form a functional entirety. T cells and B cells are the most important immunocytes in human bodies. The normal functioning of each component of the immune system provides the guarantee for the relative stability of the body immune functions, and any deficiencies or hyperactions of the component would cause damage to the body.

The components of immune system reach the whole body widely and complicatedly, particularly with the continuous production, circulation, and regeneration of the immune cells and immune molecules. The immune system possesses a great recognizability, which can precisely detect a foreign substance and distinguish it from human's own healthy tissue in order to maintain body's relative stability. Simultaneously, the immune system can accept, transfer, enlarge, depot, and memorize the related immune information, and provide positive or negative responses and regulate the responsibility to the immune information. However, the malfunctions of the immune system are disadvantageous to human body: human's abnormal recognizability easily results in allergy phenomenon, or causes iterative infections conversely; the abnormal stabilizing ability may induce the immune system to give responses to self-cells, which gives rise to autoimmune diseases.

Immunosuppressive agent is a type of new medicine category, which developed from the foundation of the research on neoplasm-chemotherapy, organ transplantation, immunopathology, and clinical immunology, etc. It possesses immunosuppressive effects which inhibits abnormal immune responses, and is generally used in the therapy of organ transplant rejection and autoimmune diseases. Common immunosuppressive agent comprises cyclophosphamide (CTX), glucocorticoid, azathioprine, cyclosporine A (CsA), rapamycin, mycophenolate mofetil and the like. Due to the restrictions of selectivity and specificity, the above mentioned immunosuppressive agents will inevitably damage immune defense capacity of the patients when receiving the treatment, resulting in the descent anti-infection ability of patients, the increasing risk of malignant lesions, the injury of hematopoietic system, immune system, liver, kidney and gastrointestinal function, neural and endocrine function disorder, and inducing some allergic reactions, etc. Therefore, the development and optimization of a new immunosuppressive agent has become an important direction for new drug development.

An agonist (such as FTY720) binds with the target molecule of sphingosine-1-phosphate receptor 1 (S1P1, a kind of GPCR), which leads to internalization of S1P1, down-regulation of the expression of S1P1 on the surface of T lymphocytes and suppression of signal transduction pathway of the target molecules. Therefore, the inflammatory immune response mediated by activated T lymphocytes is suppressed. The amino alcohol derivative has some structural similarities with the endogenous hemolytic lipid of sphingosine. Sphingosine is phosphorylated to form sphingosine-1-phosphate induced by sphingosine enzyme. Activation of the receptor leads to cells differentiation, growth and regulations of adhesion and morphology of cells. In the normal immune responses, the proliferation of T lymphocytes and B lymphocytes is taken place in lymph nodes. They down-regulate the S1P1 expression when they are in the lymph nodes. Once they are activated, the number of S1P1 on cell surface will be up-regulated, which allowed T lymphocytes and B lymphocytes to leave the lymph nodes. S1P1 on the surface of lymphocytes may bind to drugs resulting in the down-regulation of S1P1 expression, and thus losing the function of separating from the lymph nodes. To the end, lymphocytes will adhere to the lymph nodes. The amino alcohol derivative does not destroy the immune function of the lymphocytes, but make the lymphocytes remained in lymphatic system and inaccessible to blood circulatory system so that the immune response is suppressed.

Sphingosine-1-phosphate receptor 1 agonist FTY720 has been successfully developed by Novartis. However, FTY720 acts on not only sphingosine-1-phosphate receptor 1 (S1P1), but sphingosine-1-phosphate receptor 3 (S1P3), which can cause side effects such as bradycardia. Therefore, the development of S1P1 agonist with better receptor selectivity is an important research in this field.

SUMMARY OF THE INVENTION

In order to solve the technical problems in the prior art mentioned above, the present invention provides an amino alcohol derivative represented by the following Formula I, or a pharmaceutically acceptable salt, stereoisomer, isotopic label, solvate, polymorph, or prodrug thereof:

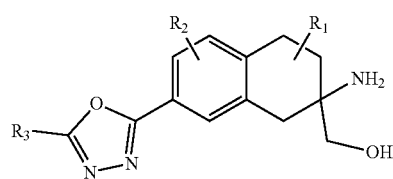

I wherein $R_1$ and $R_2$ are the same or different, and is each independently selected from H, —F, —Cl, —Br, —I, —OH, —SH, —CN, —COOH, —$NO_2$ and the following group of $C_{1-40}$ alkyl, $C_{1-40}$ alkoxy, $C_{2-40}$ alkenyl, $C_{2-40}$ alkynyl, $C_{3-20}$ cycloalkyl, $C_{3-20}$ cycloalkoxy, 3- to 20-membered heterocyclyl, 3- to 20-membered heterocycloxy, $C_{6-20}$ aryl, $C_{6-20}$ aryloxy, 5- to 20-membered heteroaryl, 5- to 20-membered heteroaryloxy, H[($CH_2$)$_n$O]$_m$—, —$NR_dR_e$, —$CONR_dR_e$ or —C(O)$Y_1R_d$, each of which is unsubstituted or optionally substituted with one or more $R_a$;

$R_3$ is selected from the group consisting of $C_{3-20}$ cycloalkyl, 3- to 20-membered heterocyclyl, $C_{6-20}$ aryl and 5- to 20-membered heteroaryl, each of which is unsubstituted or optionally substituted with one or more $R_b$;

each $R_a$ is the same as or different from any other one and is independently selected from $C_{1-40}$ alkyl, $C_{1-40}$ alkoxy, $C_{2-40}$ alkenyl, $C_{2-40}$ alkynyl, $C_{3-20}$ cycloalkyl, —F, —Cl, —Br, —I, —OH, —NH, —SH, —CN, =O or —COOH;

each $R_b$ is the same as or different from any other one and is independently selected from —F, —Cl, —Br, —I, —SH, —OH, —CN, —COOH and the following group of $C_{1-40}$ alkyl, $C_{1-40}$ alkoxy, $C_{2-40}$ alkenyl, $C_{2-40}$ alkynyl, $C_{3-20}$ cycloalkyl, 3- to 20-membered heterocyclyl, $C_{6-20}$ aryl, 5- to 20-membered heteroaryl, $C_{3-20}$ cycloalkoxy, 3- to 20-membered heterocycloxy, $C_{6-20}$ aryloxy, 5- to 20-membered heteroaryloxy, $(C_{3-20})$cycloalkyl$(C_{1-40})$alkyl, (3- to 20-membered)heterocyclyl$(C_{1-40})$alkyl, $(C_{6-20})$aryl$(C_{1-40})$alkyl, (5- to 20-membered)heteroaryl$(C_{1-40})$alkyl, $H[(CH_2)_nO]_n$—, —$NR_cR_d$, —$C(O)NR_cR_d$, —$Y_1C(O)R_e$ and —$C(O)Y_1R_e$, each of which is unsubstituted or optionally substituted with one or more $R_a$;

or, when $R_3$ is substituted with two or more identical or different $R_b$, two of which losing their hydrogen atoms or other groups respectively, are taken together with the carbon atoms to which they are attached to form a ring system $R_s$ fused with $R_3$, wherein $R_s$ is selected from $C_{3-20}$ cycloalkyl, 3- to 20-membered heterocyclyl, $C_{6-20}$ aryl, or 5- to 20-membered heteroaryl fused with $R_3$.

$R_c$, $R_d$ and $R_e$ are the same or different, each of which is independently selected from H and the following group of $C_{1-40}$ alkyl, $C_{2-40}$ alkenyl, $C_{2-40}$ alkynyl, $C_{3-20}$ cycloalkyl, 3- to 20-membered heterocyclyl, $C_{6-20}$ aryl, 5- to 20-membered heteroaryl or $CONH_2$, each of which is unsubstituted or optionally substituted with one or more $R_a$;

$Y_1$ is selected from a chemical bond, —O—, —S—, and the group of —NH—, $C_{1-40}$ alkyl, $C_{1-40}$ alkoxy, $C_{3-20}$ cycloalkyl, 3- to 20-membered heterocyclyl, $C_{6-20}$ aryl, 5- to 20-membered heteroaryl, or $(CH_2CH_2O)_j$—, each of which is unsubstituted or optionally substituted with one or more $R_a$;

m, n and j may be the same or different, each of which is independently selected from an integer equal to or more than 1, for example an integer in the range of 1 to 20, such as 1, 2, 3, 4, 5, 6, 7, 8, 9 or 10.

According to one embodiment of the present invention, wherein $R_1$ and $R_2$ may be the same or different, each of which is independently selected from H, —F, —Cl, —Br, —I, —OH, —SH, —CN, —COOH or $C_{1-40}$ alkyl, for example, $R_1$ or $R_2$ is selected from H or $C_{1-40}$ alkyl;

$R_3$ may be selected from the group consisting of $C_{3-8}$ cycloalkyl, 3- to 8-membered heterocyclyl, $C_{6-10}$ aryl and 5- to 6-membered heteroaryl, each of which is unsubstituted or optionally substituted with one or more $R_b$;

each $R_b$ is the same as or different from any other one and is independently selected from —F, —Cl, —Br, —I, —SH, —OH, —CN, —COOH and the following group of $C_{1-6}$ alkyl, $C_{1-6}$ alkoxy, $C_{3-8}$ cycloalkyl, 3- to 8-membered heterocyclyl, $C_{6-10}$ aryl, 5- to 6-membered heteroaryl, $C_{3-8}$ cycloalkoxy, 3- to 8-membered heterocycloxy, $C_{6-10}$ aryloxy, 5- to 6-membered heteroaryloxy, $(C_{3-8})$cycloalkyl$(C_{1-6})$alkyl, (3- to 8-membered)heterocyclyl$(C_{1-6})$alkyl, $(C_{6-10})$aryl$(C_{1-6})$alkyl, (5- to 6-membered)heteroaryl$(C_{1-6})$alkyl, $H[(CH_2)_nO]_n$—, —$NR_cR_d$, —$C(O)NR_cR_d$, —$Y_1C(O)R_e$ or —$C(O)Y_1R_e$, each of which is unsubstituted or optionally substituted with one or more $R_a$;

or, when $R_3$ is substituted with two or more identical or different $R_b$, two of which losing their hydrogen atoms or other groups respectively, are taken together with the carbon atoms to which they are attached to form a ring system $R_s$ fused with $R_3$, wherein $R_s$ is selected from $C_{3-8}$ cycloalkyl, 3- to 8-membered heterocyclyl, $C_{6-10}$ aryl, or 5- to 6-membered heteroaryl fused with $R_3$.

According to one embodiment of the present invention, $R_3$ may be selected from phenyl, pyridinyl, pyrazinyl, cyclohexyl, piperidinyl and piperazinyl.

As an example, $R_3$ may be selected from phenyl, pyridin-1-yl, pyridin-2-yl, pyridin-3-yl, pyridin-4-yl, piperidin-1-yl, piperidin-2-yl, piperidin-3-yl and piperidin-4-yl.

According to one embodiment of the present invention, $R_3$ could be substituted with each of $R_b$ at any suitable position, such as at position 1, 2, 3, or 4 of $R_3$.

According to one embodiment of the present invention, each $R_b$ may be the same as or different from any other one and is independently selected from —F, —Cl, —Br, —I, —SH, —OH, —CN, —COOH and the following group of $C_{1-6}$ alkyl (such as methyl, ethyl, propyl, isopropyl, t-butyl), $C_{1-6}$ alkoxy (methoxy, ethoxy, propoxy, i-propoxy, t-butoxy), $C_{3-6}$ cycloalkyl, $C_{3-6}$ cycloalkoxy, $C_{1-6}$ alkylcarbonylamino, $C_{1-6}$ alkoxycarbonal, $C_{1-6}$ alkylcarbonyloxy, (3- to 6-membered)heterocyclyl$(C_{1-6})$alkyl, —$CONH_2$, and —$NHCOCH_3$, each of which is unsubstituted or optionally substituted with one or more $R_a$.

As an example, each $R_b$ may be the same as or different from any other one and is independently selected from —F, —OH, —CN, —$CF_3$, —COOH, —$CONH_2$, methoxy, ethoxy, propoxy, i-propoxy, —$NHCOCH_3$, cyclopentyl, —$C(O)OCH_3$, 1-azetidinylmethyl, 1-pyrrolidinylmethyl and 1-piperidinylmethyl;

or, when $R_3$ is substituted with two or more identical or different $R_b$, two of which losing their hydrogen atoms or other groups respectively, are taken together with the carbon atoms to which they are attached to form a ring system $R_s$ fused with $R_3$, wherein $R_s$ is selected from dioxol ring system fused with $R_3$.

According to one embodiment of the present invention, when $R_3$ is phenyl, which is preferably substituted with $R_{b3}$ at least in position 3 and $R_{b3}$ is an electron withdrawing group.

According to a further embodiment of the present invention, when $R_3$ is phenyl, which is preferably substituted with $R_N4$ at least in position 4 and $R_N4$ is an electron donating group.

As an example, $R_{b3}$ may be selected from —Cl, —Br, —I, —SH, —OH, —CN, —COOH, —$CONH_2$, —CO—$(C_{1-6})$ alkyl, —CO—$(C_{3-6})$cycloalkyl, and —$CF_3$.

As an example, $R_{b4}$ may be selected from $C_{1-6}$ alkyl (such as methyl, ethyl, propyl, isopropyl, t-butyl), $C_{1-6}$ alkoxy (such as methoxy, ethoxy, propoxy, i-propoxy, t-butoxy), $C_{3-6}$ cycloalkyl, $C_{3-6}$ cycloalkoxy, $C_{1-6}$ alkylcarbonylamino.

According to an amino alcohol derivative represented by Formula I of the present invention, the amino alcohol derivative may have the structure of Formula I':

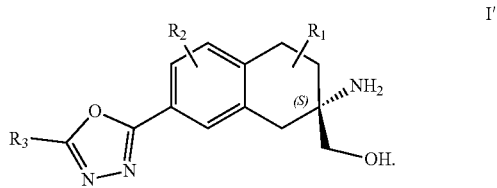

As an embodiment, the compound of Formula I in the present invention may be selected from the following compounds:
| Structure of Compounds |
|---|
| 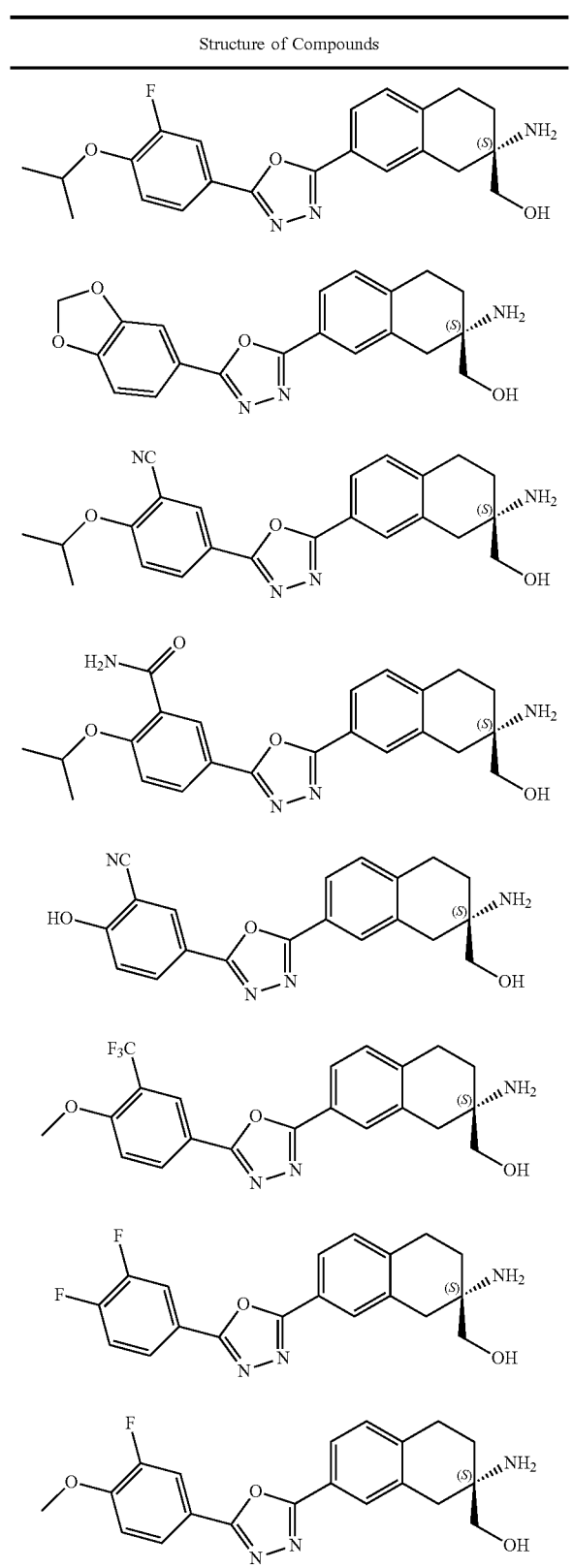 |
| -continued |
|---|
| Structure of Compounds |
| 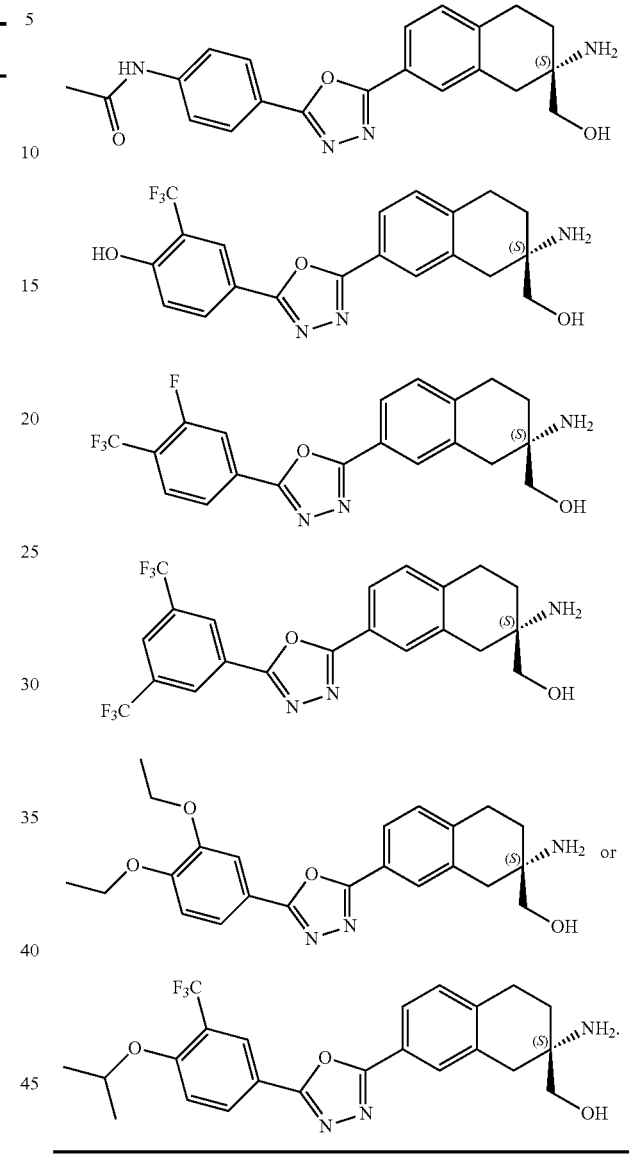 |
The present invention also provides a preparation method of the amino alcohol derivative represented by Formula I comprising one or more steps of a to f:
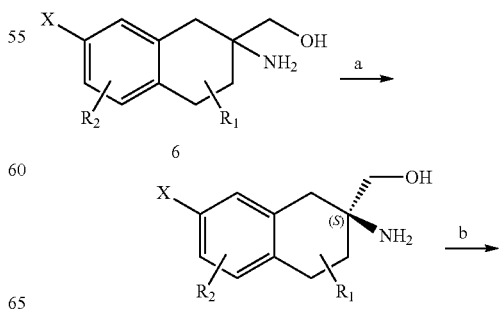

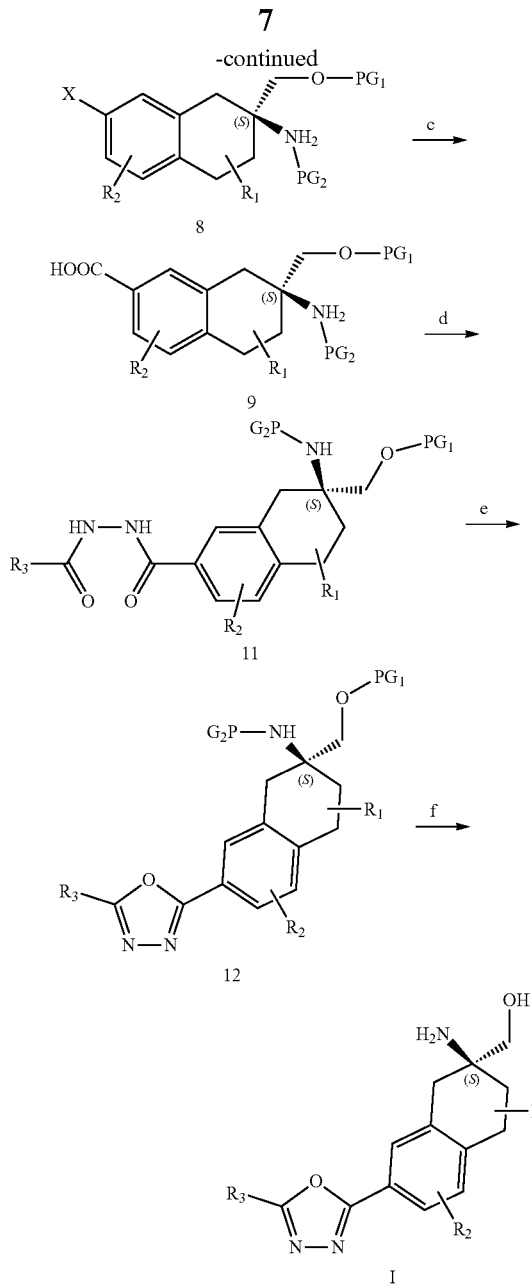

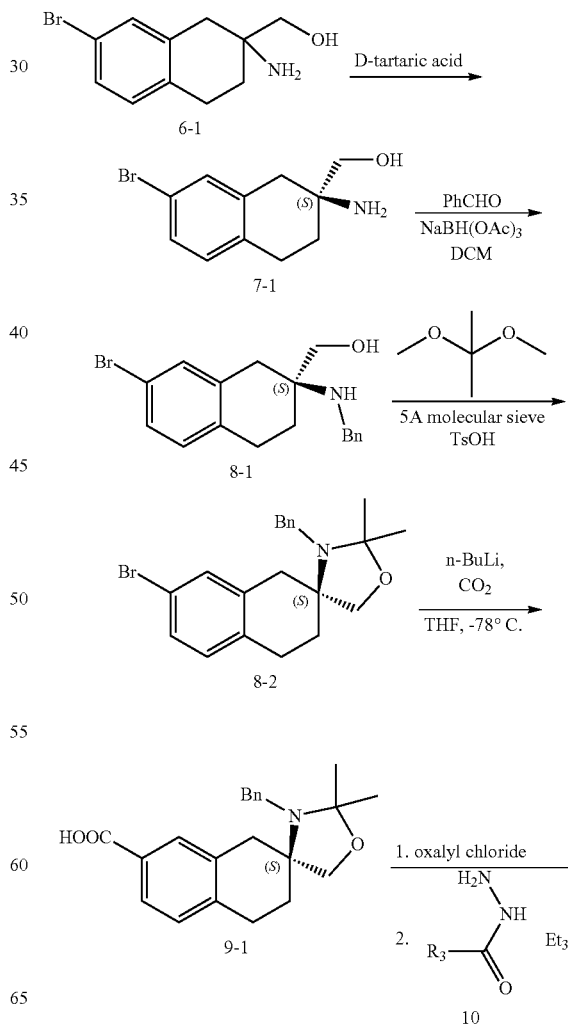

in the step d, the compound 9 may react with oxalyl chloride first, then the resultant product reacts with compound 10 represented by the following formula in the presence of triethylamine to obtain compound 11;

in the step e, the compound 11 reacts in the presence of TsCl and triethylamine to obtain compound 12;

in the step f, the hydroxyl protecting group $PG_1$ and the amino protecting group $PG_2$ are removed under conditions for deprotection, for example, the hydroxyl protecting group is removed in the presence of acid, and the amino protecting group is removed under reduction condition.

According to one embodiment of the preparation method in the present invention, the method may comprise the following steps:

wherein $R_1$, $R_2$, and $R_3$ are defined as previously;

X is selected from halogen;

$PG_1$ is selected from hydroxyl protecting groups;

$PG_2$ is selected from amino protecting groups;

or, $PG_1$ may be linked with $PG_2$ by a bond so as to protect the hydroxyl group as well as the carbonyl group.

According to one embodiment of the preparation method in the present invention, wherein:

in the step a, D-tartaric acid may be used as a resolution agent to obtain compound 7;

in the step b, the amino group of the compound 7 may be protected first in the presence of PhCHO and $NaBH(OAc)_3$, and then compound 8 is obtained in the presence of $CH_3OC(CH_3)_2OCH_3$ and acid;

in the step c, the compound 8 reacts in the presence of n-BuLi and $CO_2$ at the temperature of −78° C. to obtain compound 9;

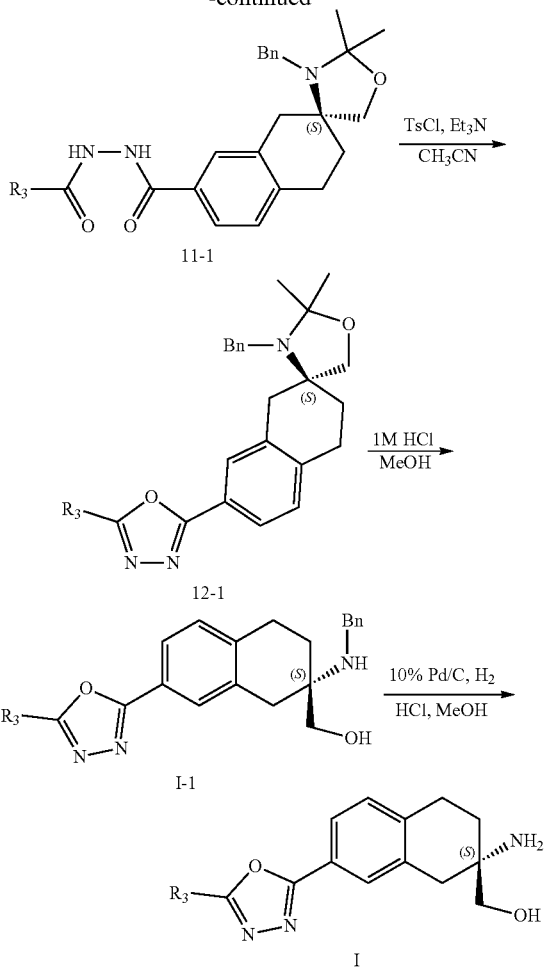

The present invention also provides a pharmaceutical composition comprising an amino alcohol derivative represented by Formula I of the present invention a pharmaceutically acceptable salt, stereoisomer, isotopic label, solvate, polymorph or prodrug thereof, and a pharmaceutically acceptable carrier.

According to the present invention, the pharmaceutical composition may comprise, but is not limited to, dosage forms for oral administration, parenteral administration, topical administration and rectal administration.

In some embodiments, the pharmaceutical composition may be in the form of tablet, capsule, pill, powder, sustained release preparation, solution or suspension for oral administration; sterile solution, suspension or emulsion for parenteral injection; ointment or cream for topical administration; or suppository for rectal administration.

In further embodiments, the pharmaceutical composition is in a unit dosage form suitable for single administration of a precise dosage.

In further embodiments, the amount of the compound is in a range of about 0.001 mg/kg body weight/day to about 1000 mg/kg body weight/day.

In further embodiments, the amount of the compound is in a range of about 0.5 mg/kg body weight/day to about 50 mg/kg body weight/day.

In some embodiments, the amount of the compound is about 0.001 g/day to about 7 g/day.

In further embodiments, the amount of the compound is about 0.002 g/day to about 6 g/day.

In further embodiments, the amount of the compound is about 0.005 g/day to about 5 g/day.

In further embodiments, the amount of the compound is about 0.01 g/day to about 5 g/day.

In further embodiments, the amount of the compound is about 0.02 g/day to about 5 g/day.

In further embodiments, the amount of the compound is about 0.05 g/day to about 2.5 g/day.

In further embodiments, the amount of the compound is about 0.1 g/day to about 1 g/day.

In further embodiments, dosage levels below the lower limit of the aforesaid ranges may be adequate.

In further embodiments, dosage levels above the upper limit of the aforesaid ranges may be required.

In some embodiments, the compound is administered in a single dose once a day.

In further embodiments, the compound is administered in multiple doses more than once a day.

In some embodiments, the compound is administered twice a day.

In further embodiments, the compound is administered three times a day.

In further embodiments, the compound is administered four times a day.

In further embodiments, the compound is administered more than four times a day.

In some embodiments, the individual to which the pharmaceutical composition is administrated is a mammal.

In further embodiments, the mammal is human.

In further embodiments, the pharmaceutical composition further comprises at least one therapeutic agent (i.e., formulated into a single dosage form).

In some embodiments, the pharmaceutical composition and the at least one therapeutic agent, respectively, in separate dosage forms, are combined into a combination product such as a kit of part.

The present invention also provides an amino alcohol derivative represented by the Formula I described above or a pharmaceutically acceptable salt, stereoisomer, isotopic label, solvate, polymorph or prodrug thereof for use in the preparation of a medicament for down-regulating S1P1 expression.

The present invention also provides an amino alcohol derivative represented by the Formula I described above or a pharmaceutically acceptable salt, stereoisomer, isotopic label, solvate, polymorph or prodrug thereof for use in down-regulating the S1P1 expression.

The present invention also provides a method for regulating (e.g., down-regulating) the activity of S1P1, comprising contacting S1P1 with an effective amount of the compound described above or a pharmaceutically acceptable salt, stereoisomer, isotopic label, solvate, polymorph or prodrug thereof.

Preferably, the method may be used in vivo, and may be also used in vitro.

The present invention also provides an amino alcohol derivative represented by the Formula I described above or a pharmaceutically acceptable salt, stereoisomer, isotopic label, solvate, polymorph or prodrug thereof for use in the preparation of a medicament for treating or preventing a disease or condition associated with immune inflammation.

The present application also provides an amino alcohol derivative represented by the Formula I described above or a pharmaceutically acceptable salt, stereoisomer, isotopic label, solvate, polymorph or prodrug thereof for use in treating or preventing a disease or condition associated with immune inflammation.

The present application also provides an amino alcohol derivative represented by the Formula I described above or a pharmaceutically acceptable salt, stereoisomer, isotopic label, solvate, polymorph or prodrug thereof for use in the preparation of a medicament for treating or preventing a disease or condition associated with immune activity.

The present application also provides a method for treating a disease or condition associated with immune activity, comprising administrating an effective amount of an amino alcohol derivative represented by the Formula I described above or a pharmaceutically acceptable salt, stereoisomer, isotopic label, solvate, polymorph or prodrug thereof to an individual in need thereof.

According to the present invention, the individual may be a mammal, such as human.

According to one embodiment of the present invention, the disease or condition associated with immune activity may be one or more of multiple sclerosis, amyotrophic lateral sclerosis, chronic inflammatory demyelinating polyradiculoneuropathy (CIDP), systemic lupus erythematosus, rheumatoid arthritis, ulcerative colitis, psoriasis, multiple myositis, type I diabetes, hyperthyroidism, scleroderma and myasthenia gravis.

Definition and Explanation of Terms

Unless defined otherwise, all technical and scientific terms used herein have the same meaning as that commonly understood by those skilled in the art to which the claimed subject belongs. All patents, patent applications and published materials referred to throughout the entire disclosure herein, unless noted otherwise, are incorporated by reference in their entirety. In the event that there is a plurality of definitions for terms herein, those in this section prevail.

It should be understood that the foregoing general description and the following detailed description are exemplary and explanatory only and are not restrictive of any subject matter claimed. In the present application, the use of the singular includes the plural unless specifically stated otherwise. It should also be noted that the use of "or" means "and/or" unless stated otherwise. Besides, use of the term "comprising" as well as other forms, such as "comprise", "comprises" and "comprised" is not limiting.

Whenever a numerical range recited in the specification and claims herein is defined as "an integer", it should be understood that both endpoints of the range and each integer within the range are recited. For example, "an integer of 0 to 10" should be understood as reciting each integer of 0, 1, 2, 3, 4, 5, 6, 7, 8, 9 and 10. When the numerical range is defined as "a number", it should be understood that both endpoints of the range, each integer within the range, and each decimal within the range are recited. For example, "a number from 0 to 10" should be understood as not only each integer of 0, 1, 2, 3, 4, 5, 6, 7, 8, 9 and 10, but also at least the sum of each of the integers and 0.1, 0.2, 0.3, 0.4, 0.5, 0.6, 0.7, 0.8 and 0.9, respectively, are recited.

It should be understood that definition of standard chemical terms may be found in reference works (including "Carey and Sundberg 'ADVANCED ORGANIC CHEMISTRY $4^{TH}$ ED.' Vols. A (2000) and B (2001), Plenum Press, New York"). Unless otherwise indicated, conventional methods, such as mass spectrum, NMR, IR, and UV/Vis spectroscopy and pharmacology methods, within the skill of the art are employed. Unless specific definitions are provided, the nomenclature employed in connection with the analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacture's specifications or as commonly accomplished in the art or as described herein. The foregoing techniques and procedures can be generally performed by conventional methods well known in the art and as described in various general and more specific references that are cited and discussed throughout the present specification. Throughout the specification, groups and substituents thereof can be chosen by one skilled in the art to provide stable moieties and compounds. Wherein substituent groups are specified by their conventional chemical formulas, written from left to right, they equally encompass the chemically identical substituents that would result from writing the structure from right to left. For example, $CH_2O$ is equivalent to $OCH_2$.

The term "optional" or "optionally" means that the subsequently described event or circumstance may or may not occur, and that the description includes instances wherein said event or circumstance occurs and instances in which it does not.

The term "halogen" refers to F, Cl, Br and I. In other words, F, Cl, Br and I could be described as halogen in the specification.

It should be understood that the term "$C_{1-40}$ alkyl" preferably refers to a monovalent radical of a straight or branched saturated hydrocarbon having 1 to 40 carbon atoms, and is preferably $C_{1-10}$ alkyl. It should be understood that "$C_{1-10}$ alkyl" preferably refers to a monovalent radical of a straight or branched saturated hydrocarbon having 1, 2, 3, 4, 5, 6, 7, 8, 9 or 10 carbon atoms. The alkyl group is, for example, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl or isomer thereof. Specifically, the group has 1, 2, 3, 4, 5 or 6 carbon atoms ("$C_{1-6}$ alkyl") such as methyl, ethyl, propyl, butyl, isopropyl, isobutyl, sec-butyl, tert-butyl. More specifically, the group has 1, 2 or 3 carbon atoms ("$C_{1-3}$ alkyl"), such as methyl, ethyl, n-propyl or isopropyl.

It should be understood that the term "$C_{2-40}$ alkenyl" preferably refers to a monovalent radical of a straight or branched hydrocarbon containing one or more double bonds and 2 to 40 carbon atoms, and is preferably $C_{2-10}$ alkenyl. It should be understood that the term "$C_{2-10}$ alkenyl" preferably refers to a monovalent radical of a straight or branched hydrocarbon containing one or more double bonds and 2, 3, 4, 5, 6, 7, 8, 9 or 10 carbon atoms, especially 2 or 3 carbon atoms ("$C_{2-3}$ alkenyl"). It should be understood when the alkenyl group comprises more than one double bond, the double bonds could be conjugated or isolated. The alkenyl group is, for example, vinyl, allyl, (E)-2-methylethenyl, (Z)-2-methylethenyl, (E)-2-butenyl, (Z)-2-butenyl, (E)-1-butenyl, (Z)-1-butenyl, 4-pentenyl, (E)-3-pentenyl, (Z)-3-pentenyl, (E)-2-pentenyl, (Z)-2-pentenyl, (E)-1-pentenyl, (Z)-1-pentenyl, 5-hexenyl, (E)-4-hexenyl, (Z)-4-hexenyl, (E)-3-hexenyl, (Z)-3-hexenyl, (E)-2-hexenyl, (Z)-2-hexenyl, (E)-1-hexenyl, (Z)-1-hexenyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylethenyl, or 1-isopropylethenyl.

It should be understood that the term "$C_{2-40}$ alkynyl" preferably refers to a monovalent radical of a straight or branched hydrocarbon having one or more triple bonds and 2 to 40 carbon atoms, and is preferably $C_{2-10}$ alkynyl. It should be understood that the term "$C_{2-10}$ alkynyl" preferably refers to a monovalent radical of a straight or branched hydrocarbon having one or more triple bonds and 2, 3, 4, 5, 6, 7, 8, 9 or 10 carbon atoms, especially 2 or 3 carbon atoms ("$C_{2-3}$ alkynyl"). The alkynyl group is, for example, ethynyl, 1-propynyl, 2-propynyl, 1-butynyl, 2-butynyl, 3-butynyl, 1-penynyl, 2-penynyl, 3-penynyl, 4-penynyl, 1-hexynyl, 2-hexynyl, 3-hexynyl, 4-hexynyl, 5-hexynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpen-4-ynyl, 2-methylpen-4-ynyl, 1-methylpen-4-ynyl, 2-methylpen-3-ynyl, 1-methylpen-3-ynyl, 4-methylpen-2-ynyl, 1-methylpen-2-ynyl, 4-methylpen-1-ynyl, 3-methylpen-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl. The alkynyl group is especially ethynyl, 1-propynyl or 2-propynyl.

It should be understood that the term "$C_{3-20}$ cycloalkyl" refers to a monovalent radical of a monocyclic or bicyclic saturated hydrocarbon ring system having 3 to 20 carbon atoms, and is preferably $C_{3-10}$ cycloalkyl. It should be understood that the term "$C_{3-10}$ cycloalkyl" refers to a monovalent radical of a monocyclic or bicyclic saturated hydrocarbon ring system having 3, 4, 5, 6, 7, 8, 9 or 10 carbon atoms. The $C_{3-10}$ cycloalkyl may be a monocyclic hydrocarbon group, for example, cyclopropyl, cyclobutyl, cyclopentyl, cyclohexyl, cycloheptyl, cyclooctyl, cyclononyl, or cyclodecyl, or may be a bicyclic hydrocarbon group such as decahydronaphthyl.

The term "3- to 20-membered heterocyclyl" refer to a monovalent radical of a monocyclic or bicyclic saturated hydrocarbon ring system having 1 to 5 ring heteroatoms, wherein each heteroatom is independently selected from N, O, and S, and is preferably 3- to 10-membered heterocyclyl. The term "3- to 10-membered heterocyclyl" refer to a monovalent radical of a monocyclic or bicyclic saturated hydrocarbon ring system having 1 to 5, preferably 1 to 3 ring heteroatoms, wherein each heteroatom is selected from N, O, and S. The heterocyclyl can be attached to the rest moiety of a chemical structure through any ring carbon atom or nitrogen atom (if present). Representative heterocyclyl groups include, but are not limited to, 4-membered heterocyclyl, such as azetidinyl, oxetanyl; 5-membered heterocyclyl, such as terahydrofuryl, dioxolyl, pyrrolidinyl, imidazolidinyl, pyrazolidinyl, pyrrolinyl; or 6-membered heterocyclyl, such as tetrahydropyranyl, piperidinyl, morpholinyl, dithianyl, thiomorpholinyl, piperazinyl, or trithianyl; or 7-membered heterocyclyl, such as diazepanyl. The heterocyclyl group may optionally be a benzofused ring system. The heterocyclyl group may be bicyclic, for example but not limited to 5,5-membered bicyclic ring, such as hexahydrocyclopenta[c]pyrrol-2(1H)-yl, or 5,6-membered bicyclic ring, such as hexahydropyrrolo[1,2-a]pyrazin-2(1H)-yl. The ring system containing nitrogen atom(s) may be partially unsaturated, therefore it may contain one or more double bonds, for example but is not limited to 2,5-dihydro-1H-pyrrolyl, 4H-[1,3,4]thiadiazinyl, 4,5-dihydrooxazolyl or 4H-[1,4]thiazinyl, or may be a benzofused ring system, for example but is not limited to dihydroisoquinolinyl, 1,3-benzoxazolyl, 1,3-benzodioxolyl. According to the present invention, the heterocyclyl groups have no aromaticity.

It should be understood that the term "$C_{6-20}$ aryl" refers to a monovalent radical of a mono-, bi-, or tri-cyclic hydrocarbon ring system in which the whole or part of the structure is aromatic, and is preferably "$C_{6-14}$ aryl". It should be understood that the term "$C_{6-14}$ aryl" is preferably a monovalent radical of a mono-, bi-, or tri-cyclic hydrocarbon ring system in which the whole or part of the structure is aromatic, having 6, 7, 8, 9, 10, 11, 12, 13, or 14 carbon atoms ($C_{6-14}$ aryl). Specially, $C_{6-14}$ aryl is a ring having 6 carbon atoms ($C_6$ aryl), such as phenyl, or biphenyl; or a ring having 9 carbon atoms ($C_9$ aryl), such as indanyl or indenyl; or a ring having 10 carbon atoms ($C_{10}$ aryl), such as tetrahydronaphthalenyl, dihydronaphthalenyl or naphthyl; or a ring having 13 carbon atoms ($C_{13}$ aryl), such as fluorenyl; or a ring having 14 carbon atoms ($C_{14}$ aryl), such as anthryl.

It should be understood that the term "5- to 20-membered heteroaryl" comprises a monovalent radical of a mono-, bi-, or tri-cyclic aromatic ring system having 5 to 20 ring atoms of which 1 to 5 ring atoms are independently selected from N, O and S, such as "5- to 14-membered heteroaryl". It should be understood that the term "5- to 14-membered heteroaryl" comprises a monovalent radical of a mono-, bi-, or tri-cyclic aromatic ring system having 5, 6, 7, 8, 9, 10, 11, 12, 13, or 14 ring atoms, especially 5, 6, 9 or 10 carbon atoms, of which 1 to 5, preferably 1 to 3 ring atoms are independently selected from N, O and S, and may be a benzofused ring in any situation. The heteroaryl is especially selected from thienyl, furyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl and benzo derivatives thereof, for example, benzofuranyl, benzothiophenyl, benzoxazolyl, benzisoxazolyl, benzimidazolyl, benzotriazolyl, indazolyl, indolyl, isoindolyl; or pyridyl, pyridazinyl, pyrimidinyl, pyrazinyl, triazinyl and benzo derivatives thereof, for example, quinolyl, quinazolinyl, isoquinolyl; or azocinyl, indolizinyl, purinyl and benzo derivatives thereof, or cinnolinyl, phthalazinyl, quinazolinyl, quinoxalinyl, naphthyridinyl, pteridyl, carbazolyl, acridinyl, phenazinyl, phenothiazinyl, phenoxazinyl and the like.

Unless otherwise indicated, the heterocyclyl, heteroaryl, or heteroarylene groups comprise all possible isomeric forms, such as position isomers. Therefore, as non-limiting examples for description, pyridyl or pyridylidene comprises 2-pyridyl, 2-pyridylidene, 3-pyridyl, 3-pyridylidene, 4-pyridyl and 4-pyridylidene; thienyl or thienylidene comprises 2-thienyl, 2-thienylidene, 3-thienyl and 3-thienylidene.

The definitions of the term "alkyl" above-mentioned, such as "$C_{1-40}$ alkyl", equally apply to the terms comprising $C_{1-40}$ alkyl, for example "$C_{1-40}$ alkoxy", "$C_{1-40}$ alkylsilyl", "$C_{1-40}$ alkylsiloxy" and the like. Similarly, the definitions above-mentioned of the terms "$C_{2-40}$ alkenyl", "$C_{2-40}$ alkynyl", "$C_{3-20}$ cycloalkyl", "$C_{5-20}$ cycloalkenyl", "3- to 20-membered heterocyclyl", "$C_{6-20}$ aryl" and "5- to 20-membered heteroaryl" equally apply to the terms comprising these terms, such as "$C_{2-40}$ alkenoxy", "$C_{2-40}$ alkynoxy", "$C_{3-20}$ cycloalkoxy", "3- to 20-membered heterocyclyl", "3- to 20-membered heterocycloxy", "$C_{6-20}$ aryloxy", "$C_{6-20}$ arylalkyl", "5- to 20-membered heteroarylalkyl" and the like.

The term "protecting group" of the present invention refers to a temporary substituent used for protecting a reactive group against undesired chemical conversion. In any method for preparing the compound of the present invention, it may be necessary and/or desired to protect a sensitive or reactive group of any related molecule, which may be performed relying on a known protecting group, such as the protecting group described in a textbook or reference book in the art. The protecting group may be removed in a suitable step followed by using a known method in the art. It should be known for those skilled in the art that other reagents may be used in the deprotection step depending on the kind of the protecting group, which comprise but not limited to Pd/C, $Pd(OH)_2$, $PdCl_2$, $Pd(OAc)_2/Et_3SiH$, Raney nickel, appropriate acid, appropriate base, fluoride and the like.

The relevant terms "subject", "patient" or "individual" as used herein refer to an individual suffering from a disease, disorder or condition, and encompasses mammals and non-mammals. Examples of mammals include, but are not limited to, any member of the mammalian class: humans, non-human primates such as chimpanzees and other apes and monkeys; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fishes, and the like. In one embodiment of the method and composition provided herein, the mammal is a human.

The terms "treat," "treating" or "treatment" as used herein and other similar synonyms include alleviating, abating or ameliorating a symptom of a disease or condition, preventing other symptoms, ameliorating or preventing the underlying metabolic causes of a symptom, inhibiting a disease or condition, e.g., arresting the development of the disease or condition, relieving the disease or condition, causing improvement of the disease or condition, relieving a symptom caused by the disease or condition, or stopping a symptom of the disease or condition. In addition, the term encompasses a purpose of prophylaxis. The term further includes achieving a therapeutic benefit and/or a prophylactic benefit. By therapeutic benefit it is meant to eradicate or ameliorate the underlying disorder being treated. Furthermore, the eradication or amelioration of one or more physiological symptoms associated with the underlying disorder is also a therapeutic benefit; for example, an improvement is observed in the patient, notwithstanding that the patient may still be affected by the underlying disorder. For the prophylactic benefit, the composition may be administered to a patient at risk of developing a particular disease, or to a patient reporting one or more physiological symptoms of a disease, even though a diagnosis of this disease may not have been made.

The terms "effective amount", "therapeutically effective amount" or "pharmaceutically effective amount" as used herein refer to a sufficient amount of at least one agent or compound being administered which will relieve to some extent one or more symptoms of the disease or condition being treated. The result can be reduction and/or alleviation of the signs, symptoms or causes of a disease, or any other desired alteration of a biological system. For example, an "effective amount" for therapeutic uses is the amount of the composition comprising a compound as disclosed herein required to provide a clinically significant alleviation of a disease. An effective amount suitable for any individual case may be determined using techniques such as a dose escalation study.

The terms "administer", "administering", "administration", or the like, as used herein, refer to a method that may be used to deliver a compound or a composition to the desired site of biological action. These methods include, but are not limited to, oral route, transduodenal route, parenteral injection (including intravenous, subcutaneous, intraperitoneal, intramuscular, intra-arterial injection or infusion), topical and rectal administration. A person skilled in the art is familiar with the techniques for employing the compound and method described herein, e.g., those discussed in Goodman and Gilman, The Pharmacological Basis of Therapeutics, current ed.; Pergamon and Remington's, Pharmaceutical Sciences (current edition), Mack Publishing Co., Easton, Pa. In preferred embodiments, the compound and composition described herein are administered orally.

The term "acceptable" as used herein with respect to a formulation, composition or ingredient means having no persistent detrimental effect on the general health of the subject being treated.

The term "pharmaceutically acceptable" as used herein, refers to a material, such as a carrier or diluents, which does not affect the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition" as used herein, refers to a biologically active compound, optionally mixed with at least one pharmaceutically acceptable chemical component, such as, but not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "pharmaceutically acceptable salt" as used herein, refers to salts that retain the biological effectiveness of the free acids and bases of the specified compound and that are not biologically or otherwise undesirable. The compound of the invention also includes a pharmaceutically acceptable salt. The pharmaceutically acceptable salt refers to those formed by converting basic groups in the parent compound into a salt form. The pharmaceutically acceptable salt includes, but not limited to, inorganic or organic acid salts of the basic groups such as amine (amino) groups. The pharmaceutically acceptable salt of the invention may be synthesized from the parent compound, i.e., by reaction of the basic groups in the parent compound with 1-4 equivalents of an acid in a solvent system. Suitable salts are listed in Remington's Pharmaceutical Sciences, $17^{th}$ ed., Mack Publishing Company, Easton, Pa., 1985, p. 1418 and Journal of Pharmaceutical Science, 66, 2(1977), such as hydrochloride salt.

Unless indicated specifically, the salt of the invention refers to acidic salts formed by organic/inorganic acids, and basic salts formed by organic/inorganic bases. In addition, when the basic functional group in the compound of formula I is (but not limited to) pyridine or imidazole, and the acidic function group is (but not limited to) carboxylic acid, an amphoteric ion (an inner-salt) will be formed. The inner-salts are also encompassed in the salts of the invention.

The term "solvate" as used herein refers to a combination of a compound of this invention with a solvent molecule formed by solvation. In some embodiments, the solvate refers to a hydrate, i.e., the solvent molecule is water molecule, and the combination of a compound of this invention and water forms a hydrate. One or more compounds of the invention may exist in the form of a solvate, just like the solvates formed with the pharmaceutically acceptable solvents such as water, ethanol, and the like. Therefore, the invention includes both solvated and non-solvated forms. "Solvate" refers to a physical aggregate formed with a compound of the invention and one or more solvent molecules. This physical aggregate includes different degrees of ions and covalent bonds, for example, hydrogen bonds. It has been confirmed that this solvate may be separated off, for example, when the lattice of a crystal has one or more solvent molecules. "Solvate" includes both parts of solvent phase and separable solvate. There are many examples of the corresponding solvates, including ethanol solvate, methanol solvate, and the like. "Hydrate" is a solvate in which the solvate is water ($H_2O$) molecule.

One or more compounds of the invention may be arbitrary prepared into a solvate. The preparation of a solvate is well known in the art. For example, the preparation of a solvate of the antifungal drug, fluconazole, i.e., with ethyl acetate and water, is described in M. Caira et al, J. Pharmaceutical Sci., 93(3), 601-611 (2004). Similar preparation methods of solvates and hydrates are also described in E. C. van Tonder et al, AAPS PharmSciTech., 5(1), article 12 (2004), and A. L. Bingham et al, Chem. Commun., 603-604 (2001). A typical, non-limiting preparation process is to dissolve the compound of the invention in a desired amount of an ideal solvent (organic solvent or water or a mixture thereof) at a temperature higher than normal temperature, cool, stand and crystallize, and then separate off the crystals using a standard method. The presence of the solvent (water) in the solvate (hydrate) formed during the crystallization can be confirmed by an I.R. spectroscopic analysis technology.

The terms "polymroph" or "polymrophism" as used herein refer to a compound of this invention present in different crystal lattice forms.

The term "an isotopic label" as used herein, refers to a compound of the invention labelled by an isotope. For example, the isotopes in the compound of the invention include various isotopes of H, C, N, O, P, F, and S, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}S$.

The term "pharmaceutically acceptable prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly preferred derivatives or prodrugs are those that increase the bioavailability of the compounds of this invention when such compounds are administered to a patient (e.g., by allowing orally administered compound to be more readily absorbed into blood), or those that enhance delivery of the parent compound to a biological organ or action site (e.g., the brain or lymphatic system).

Various forms of prodrugs are well known in the art. See, T. Higuchi and V. Stella, Pro-drugs as Novel Delivery Systems (1987) Vol. 14 of the A.C.S. Symposium Series, Bioreversible Carriers in Drug Design, (1987) Edward B. Roche, ed., American Pharmaceutical Association and in Pergamon Press for discussion concerning prodrugs. *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference.

"Stereoisomer" as used herein, refers to isomers produced from different arrangements of atoms in molecules in space. The compound of formula I posses asymmetric or chiral centers, and thus different stereoisomeric forms exist. All stereostructures of molecular formula I, like a mixture, include racemic mixtures, as a part of the present invention. Diastereomer isomers can be separated into individual diastereomers, depending on their different physicochemical properties, by using the well-known means. For example, the resolution of individual enantiomers may be achieved by reacting with suitable optically active substance (for example, chiral alcohol or Mosher's acyl chloride) to convert into diastereomers, and then separating them and converting (such as hydrolyzing) into the corresponding individual isomers. Some compounds of formula I may be atropisomers (such as substituted aryl), which is also a part of the invention. Enantiomers may be isolated by using a chiral chromatographic column. The compound of formula I may exist different tautomeric forms, which are encompassed in the scope of the invention, for example, compounds in keto-enol and imine-enamine forms.

"The disease associated with immune activity" as used herein, refers to a disease caused by immune problems mainly including the following diseases: multiple sclerosis, amyotrophic lateral sclerosis, CIDP, systemic lupus erythematosus, rheumatoid arthritis, ulcerative colitis, psoriasis, multiple myositis, type I diabetes, hyperthyroidism, scleroderma, myasthenia gravis and the like.

Beneficial Effects of the Present Invention

The compound of the present invention can effectively target sphingosine-1-phosphate receptor-1 (S1P1). The side effects, such as bradycardia, are relieved when the compound of the present invention target sphingosine-1-phosphate receptor-3 (S1P3). In addition, the preparation method of the invention has a simple process, mild reaction conditions and a high product yield.

DETAILED DESCRIPTION

Hereinafter, the compound of formula I, preparation method and application thereof of the present invention will be described in more detail through the examples. It is understood that the following examples are merely exemplary descriptions and explanations, and should not be construed as limiting the scope of the present invention. Solutions obtained by a person skilled in the art based on the contents above mentioned of the invention are all covered in the scope of protection of the present invention.

Unless otherwise indicated, the starting materials and reagents in the following examples were all commercially available products, or were prepared by the methods known in the art.

The conditions for LC-MS analysis in the synthesis process are as follows:
Instrument: Agilent LCMS1260/MSD6120;
Chromatographic column: Agilent SB-C18, 2.1*50 mm, 1.8 μm, SN: USWEY07289;
Mobile phase: A: $H_2O$ (0.1% FA) 90%, B: acetonitrile 10%, 0.400 ml/min, 45.00° C.

Schedule

| Time | Function | Parameters | | |
|---|---|---|---|---|
| 2.24 | Changing solvent components | Solvent components | A: 0.0% | B: 100.0% |
| 3.00 | Changing solvent components | Solvent components | A: 0.0% | B: 100.0% |
| 3.01 | Changing flow rate | Flow rate: 0.5 ml/min | | |
| 3.01 | Changing solvent components | Solvent components | A: 90.0% | B: 10.0% |
| 5.00 | Changing solvent components | Solvent components | A: 90.0% | B: 10.0% |
| 5.01 | Changing flow rate | Flow rate: 0.4 ml/min | | |
| 5.01 | Changing solvent components | Solvent components | A: 90.0% | B: 10.0%. |

Instrument Parameters:
Ionization Mode: API-ES
Polarity: Positive
Collision-induced dissociations ascending order: Disabled
Percentage of cycle time: 50.00%.

Preparation Example 1

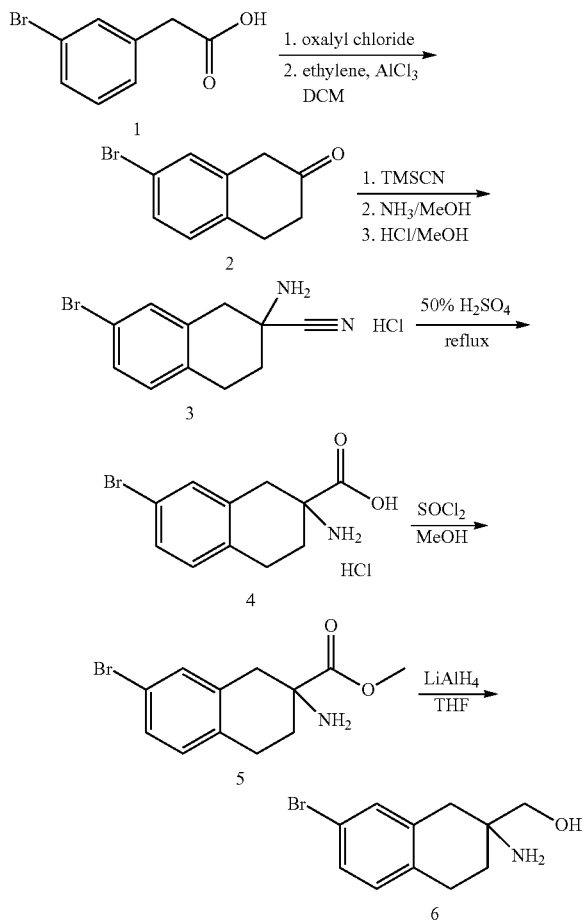

Synthesis of Intermediate 2

100 g (465 mmol) of compound 1 was dissolved in 500 ml of dichloromethane, cooled to 0° C. in ice-salt bath, and added dropwise with 120 g (930 mmol) of oxalyl chloride. After the dropping was finished, the mixture obtained was heated at reflux and reacted for 2 h. The reaction was monitored by TLC. After the reaction was completed, the solvent was evaporated to dryness, and dichloromethane was added and evaporated to dryness again to afford 112 g of intermediate, as a yellow liquid which was used directly in the next step. 210 g (1410 mmol) of aluminum chloride was suspended in 400 ml of dichloromethane, cooled to −10° C. to −5° C., and then added dropwise with a solution of 112 g of the above intermediate in 100 ml of dichloromethane. After the dropping was finished, ethylene gas was introduced into the reaction system for about 2 h keeping the temperature of −10° C. to −5° C. After TLC showed that the reaction was completed, the reaction solution was poured into ice-water mixture and extracted with dichloromethane. The organic phases were combined, washed twice with saturated sodium bicarbonate solution and once with saturated sodium chloride solution, dried, and evaporated to dryness to give a crude product, which was purified with silica gel column (eluent: petroleum ether/ethyl acetate=5/1, v/v) to give a product (85 g) as an orange-red liquid. Yield: 81.7%. LC-MS: 225, 227 $[M+1]^+$, $t_R$=2.153 min.

Synthesis of Intermediate 3

Under the protection of nitrogen, 25.5 g (113 mmol) of intermediate 2 was dissolved in 20 ml of dichloromethane, added with 1.78 g (5.6 mmol) of zinc iodide, and added dropwise with 20.7 ml (167 mmol) of trimethylsilyl cyanide under cooling in a water bath. The resulting mixture was stirred and reacted for 3 h at room temperature. The reaction was monitored by TLC. After the reaction was completed, a solution (80 ml, 20%) of ammonia in methanol was added and stirred for 3 days at room temperature. The reaction was stopped and the reaction solution was evaporated to dryness. A solution (100 ml, 11%) of hydrogen chloride in methanol was added to the residual. The mixture was stirred for 30 min, then added with 400 ml of methyl tert-butyl ether, stirred for 30 minutes again and filtered to give a product (27.9 g) as a light yellowish-white solid. Yield: 85.5%. LC-MS: 251, 253 $[M+1]^+$, $t_R$=1.731 min.

Synthesis of Intermediate 4

30 g (102 mmol) of intermediate 3 was suspended in 150 ml of sulphuric acid (50%, v:v), heated to 150° C. and reacted for 3 h. After HPLC showed that the reaction was completed, the mixture obtained was cooled to room temperature, placed in a refrigerator at 4° C. overnight and filtered. The filter cake was washed with concentrated hydrochloric acid and pumped to dryness in a dryer to give a product (32 g), as a light brown solid. Yield: 100%. LC-MS: 270, 272 $[M+1]^+$, $t_R$=1.382 min.

Synthesis of Intermediate 5

12.1 g (102 mmol) of thionyl chloride was added to 200 ml of methanol at 0° C., stirred for 1 h, then added with 25 g (34 mmol) of intermediate 4, heated at reflux and reacted for 15 h. The reaction was monitored by HPLC. After the reaction was completed, the reaction solution was evaporated to dryness and adjusted pH to 8 with saturated sodium bicarbonate solution. The aqueous phase was extracted with dichloromethane. The organic phases were combined, dried and evaporated to dryness to give a product (9 g) as a reddish brown oily substance. Yield: 91.1%. LC-MS: 284,286 $[M+1]^+$, $t_R$=1.507 min.

Preparation of Intermediate 6: (2-amino-7-bromo-1,2,3,4-tetrahydronaphthalen-2-yl)methanol 4.8 g (126 mmol) of lithium aluminium hydride was suspended in 200 ml of tetrahydrofuran, cooled to −10° C., added dropwise with a solution of 18 g (63 mmol) of intermediate 5 in 100 ml of tetrahydrofuran and then reacted for 30 min at −10° C. The reaction was monitored by TLC. After the reaction was completed, 4.8 ml of water, 14.4 ml of sodium hydroxide solution (10%) and 24 ml of water were added sequentially to the reaction system. The mixture was stirred for 20 min, then added with 70 g of anhydrous sodium sulfate, stirred for 30 minutes and allowed to stand overnight. The resulting mixture was filtered, dried and evaporated to dryness to give a product (17 g) as a black oily substance. Yield: 100%. LC-MS: 256, 258 [M+1]$^+$, $t_R$=1.143 min.

Preparation of Intermediate 7-1: (S)-(2-amino-7-bromo-1,2,3,4-tetrahydronaphthalen-2-yl)methanol The racemic mixture of intermediate 6 was separated by recrystallization process with D-tartaric acid many times until specific rotation of the product no longer increased to give chiral intermediate 7-1. Specific Rotation $[\alpha]_D^{20}$=27 (C=1, MeOH). LC-MS: 256,258 [M+1]$^+$, $t_R$=1.143 min.

Synthesis of Intermediate 8-1

17 g (66 mmol) of intermediate 7-1 and 7.75 g (73 mmol) of benzaldehyde were dissolved in 200 ml of dichloromethane, added with 6 g (99.6 mmol) of acetic acid, stirred for 1 hour, added with 21.1 g (99.6 mmol) of sodium triacetoxyborohyride in batches in an ice-salt bath, and then reacted for 2 h at room temperature. The reaction was monitored by TLC. After the reaction was completed, the reaction system was adjusted to pH 8 with saturated sodium bicarbonate solution. The aqueous phase was extracted with dichloromethane. The organic phases were combined, dried and evaporated to dryness to give a crude product, which was purified with silica gel column (eluent: petroleum ether/ethyl acetate=10/1, v/v) to give a product (15.6 g) as a black oily substance. Yield: 73%. LC-MS: 346, 348 [M+1]$^+$, $t_R$=1.821 min.

Synthesis of Intermediate 8-2

15.6 g (45 mmol) of intermediate 8-1 was dissolved in 120 ml of 2,2-dimethoxypropane, added with 1 g (5.8 mmol) of p-toluenesulfonic acid monohydrate and 10 g of molecular sieve, heated to 135° C. under confinement and reacted for 16 h. The reaction was monitored by TLC. After the reaction was completed, the resulting mixture was filtered, evaporated to dryness, added with saturated sodium bicarbonate solution and extracted with dichloromethane. The organic phases were combined, dried and evaporated to dryness to give a crude product, which was purified with silica gel column (eluent: petroleum ether/ethyl acetate=30/1, v/v) to give a product (13 g) as a faint yellow solid. Yield: 75.1%. LC-MS: 386, 388 [M+1]$^+$, $t_R$=3.352 min.

Synthesis of Intermediate 9-1

14 g (36 mmol) of intermediate 8-2 was dissolved in 100 ml of tetrahydrofuran, cooled to −78° C. under the protection of nitrogen and added dropwise with 17 ml (43.5 mmol) of n-butyllithium. The resulting mixture was stirred for 30 min at −78° C., then introduced with carbon dioxide gas for 30 minutes and naturally warmed to room temperature. The reaction was monitored by TLC. After the reaction was completed, the reaction solution was adjusted to pH 5-6 with acetic acid and evaporated to dryness to give a crude product, which was purified with silica gel column (eluent: petroleum ether/ethyl acetate=30/1, v/v) to give a product (9.1 g) as a yellowish-white solid. Yield: 71.9%. LC-MS: 352 [M+1]$^+$, $t_R$=2.415 min.

Synthesis of Intermediate 17

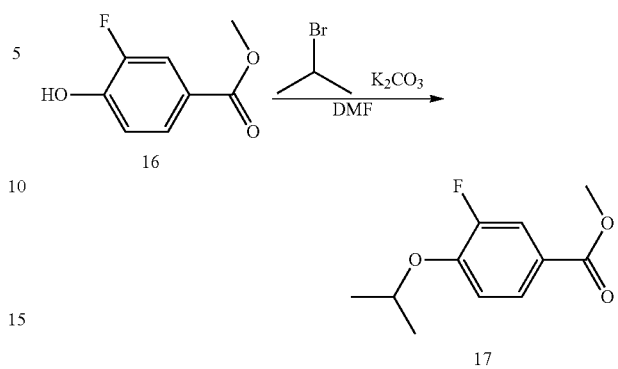

0.8 g (4.7 mmol) of material 16, 2.6 g (18.8 mmol) of potassium carbonate and 1.8 ml (18.8 mmol) of 2-bromopropane were suspended in 8 ml of DMF and reacted at 100° C. for 1 h. The reaction was monitored by TLC (PE/EA=3:1). After the reaction was completed, 30 ml of saturated sodium bicarbonate solution and 30 ml of ethyl acetate were added to the resulting mixture, which was stirred, allowed to stand, and separated. The organic phase was washed with 2×30 ml of water, dried and evaporated to dryness to give a crude product, as a brown liquid (0.94 g). Yield: 93.7%.

Synthesis of Intermediate 19

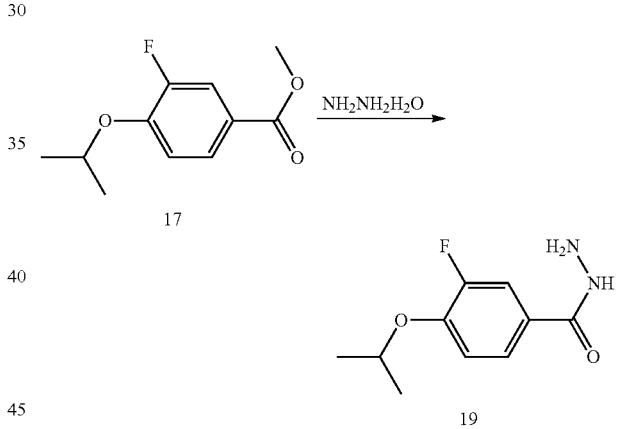

Under the protection of nitrogen, 0.94 g (4.4 mmol) of intermediate 17 was suspended in 3.2 g (52.9 mmol, 85%) of hydrazine hydrate, and reacted at 85° C. for 500 min. The reaction was monitored by TLC (PE/EA=1:1+Et$_3$N). After the reaction was completed, the resulting mixture was cooled to room temperature, filtered, washed with water, and pumped to dryness to give a white solid (0.86 g). Yield: 91.7%. LC-MS: 213 [M+1]$^+$, $t_R$=2.441 min.

Synthesis of Intermediate 21

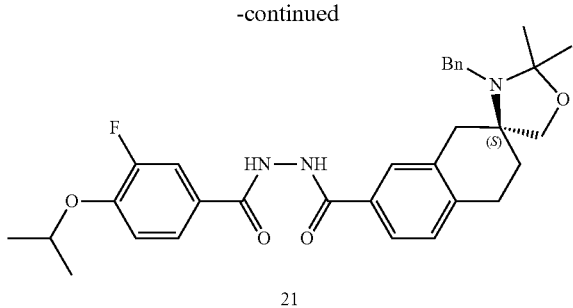

21

0.9 g (2.56 mmol) of intermediate 9-1 was dissolved in 36 ml of dichloromethane, added with 0.015 ml (cat.) of N,N-dimethylformamide and cooled to 0° C. 0.65 ml (7.68 mmol) of oxalyl chloride was added dropwise to the mixture, then naturally warmed to room temperature and reacted for 1 h. After the reaction was completed, the reaction solution was concentrated and added with 16 ml of dichloromethane, as a stock solution. 0.82 g (3.84 mmol) of compound 19 and 1.1 ml (7.68 mmol) of triethylamine were dissolved in 16 ml of dichloromethane, cooled to 0° C., added dropwise with the solution of acyl chloride in dichloromethane obtained above, then naturally warmed to room temperature and reacted overnight. The reaction was monitored by TLC (PE/EA=3:1+AcOH). After the reaction was completed, 40 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (1.2 g) as a yellow solid. Yield: 84.8%. LC-MS: 546 [M+1]$^+$, $t_R$=4.125 min.

Synthesis of Intermediate 22

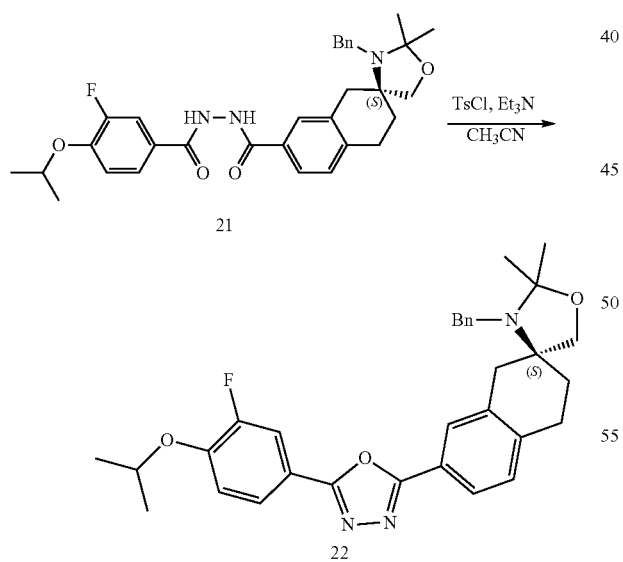

1.2 g (2.16 mmol) of intermediate 21 and 1 ml (6.49 mmol) of triethylamine were dissolved in 24 ml of acetonitrile, cooled to 0° C., added with 0.62 g (3.24 mmol) of 4-toluene sulfonyl chloride, and stirred overnight at room temperature. The reaction was monitored by TLC (PE/EA=1:1). After the reaction was completed, water was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=10/1, v/v) to give a product (0.7 g) as a white solid. Yield: 61.4%. LC-MS: 528 [M+1]$^+$, $t_R$=5.226 min.

Synthesis of Intermediate 23

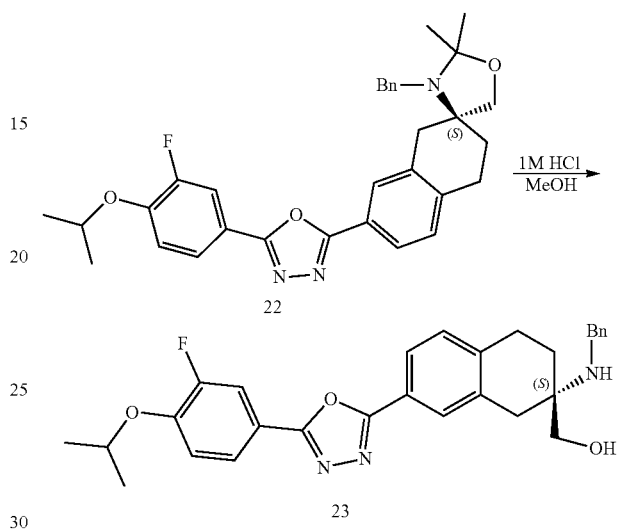

0.7 g (1.33 mmol) of intermediate 22 was dissolved in 3.7 ml of hydrochloric acid (1 M) and 21 ml of methanol, and reacted for 120 min at 80° C. The reaction was monitored by TLC (PE/EA=1:1+Et$_3$N). After the reaction was completed, the resulting mixture was concentrated by rotary evaporation, added with 20 ml of saturated sodium bicarbonate solution and 20 ml of dichloromethane, and separated into layers. The aqueous phase was extracted with dichloromethane. The organic phases were combined, dried and rotary evaporated to dryness to give a crude product, which was purified with silica gel column (eluent: petroleum ether/ethyl acetate=1/2+1% Et$_3$N, v/v) to give a product (0.6 g) as a white solid. Yield: 94.0%.

Example 1 (S)-(2-amino-7-(5-(3-fluoro-4-isopropoxyphenyl)-1,3,4-oxadiazol-2-yl)-1,2,3,4-tetrahydronaphthalen-2-yl)methanol

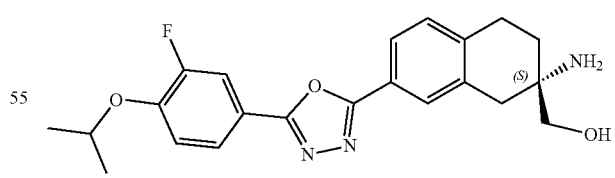

0.6 g (1.24 mmol) of intermediate 23 was dissolved in 13 ml of methanol, added with 0.01 ml of concentrated hydrochloric acid, purged with nitrogen to remove air, followed by the addition of 0.122 g (20% m/m) of palladium 10% on carbon, purged with hydrogen, and reacted for 240 min at 95° C. The reaction was monitored by TLC (DCM:MeOH=10:1). After the reaction was completed, the resulting mixture was filtered, and the filter cake was washed with plenty of methanol. The filtrate was concentrated by rotary evaporation, added with 30 ml of saturated sodium bicarbonate solution and 30 ml of dichloromethane, stirred, allowed to stand and separated into layers. The aqueous phase was extracted with dichloromethane. The organic phases were combined, dried, filtered and rotary evaporated to give a crude product, which was purified with silica gel column (eluent: DCM:MeOH=10/1+1% Et$_3$N, V/V) to give the target compound of Example 1 as a white solid (0.3 g). Yield: 61.89%. LC-MS: 398 [M+1]$^+$, t$_R$=3.090 min. A corresponding hydrogenchloride salt was obtained by mixing the solid with a solution of hydrogen chloride in methanol under stirring.

Preparation Example 2

Synthesis of Intermediate 27

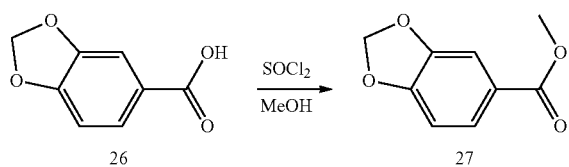

2.0 g (12 mmol) of intermediate 26 was dissolved in 20 ml of methanol, cooled to 0° C., added dropwise with 2.6 ml (36 mmol) of thionyl chloride, warmed to room temperature, stirred and reacted overnight. The reaction was monitored by TLC. After the reaction was completed, the reaction solution was adjusted to pH 8 with saturated sodium bicarbonate solution, and rotary evaporated to dryness to remove methanol. The aqueous phase was extracted with dichloromethane. The organic phases were combined, dried and rotary evaporated to dryness to give a product (1.9 g) as a white solid. Yield: 81.67%.

Synthesis of Intermediate 28

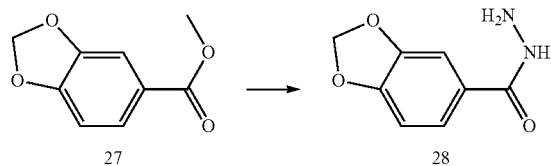

Under the protection of nitrogen, 1.911 g (9.8 mmol) of intermediate 27 was dissolved in 7 g (118.7 mmol, 85%) of hydrazine hydrate, heated to 85° C. and reacted for 7 h. The reaction was monitored by TLC. After the reaction was completed, the resulting mixture was cooled to room temperature, filtered and pumped to dryness to give a white solid (1.728 g). Yield: 81.67%.

Synthesis of Intermediate 29

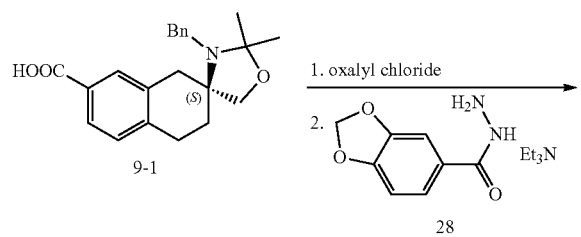

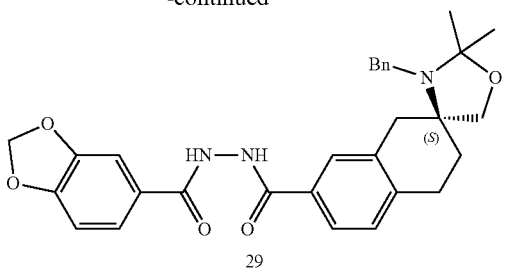

1.0 g (2.84 mmol) of intermediate 9-1 was dissolved in 40 ml of dichloromethane, added with 5 drops of N,N-dimethylformamide and cooled to 0° C. 0.72 ml (8.52 mmol) of oxalyl chloride was added dropwise to the mixture, then naturally warmed to room temperature and reacted for 1 hour. After the reaction was completed, the reaction solution was concentrated and added with 30 ml of dichloromethane, as a stock solution. 0.823 g (8.52 mmol) of compound 28 and 1.19 ml (8.52 mmol) of triethylamine were dissolved in 30 ml of dichloromethane and cooled to 0° C. The solution of acyl chloride in dichloromethane obtained above was added dropwise to the mixture, then naturally warmed to room temperature and reacted overnight. The reaction was monitored by TLC (PE/EA=3:1+AcOH). After the reaction was completed, 500 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (1.3 g) as a yellow solid. Yield: 89.08%. LC-MS: 514 [M+1]$^+$, t$_R$=8.349 min.

Synthesis of Intermediate 30

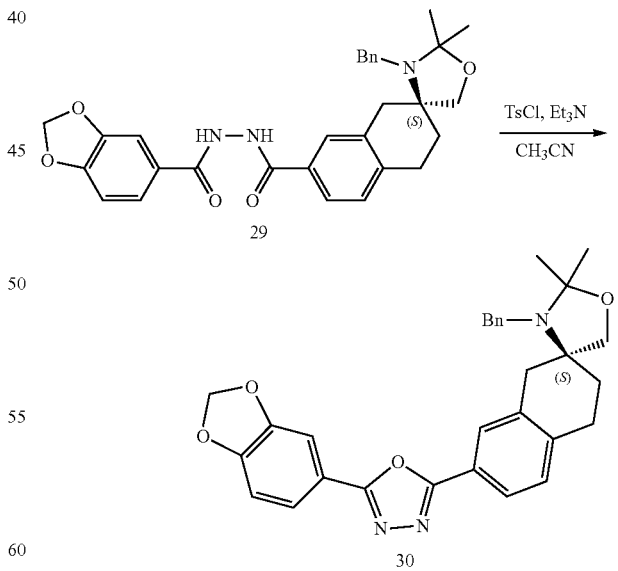

1.3 g (2.53 mmol) of intermediate 29 and 1.06 ml (7.60 mmol) of triethylamine were dissolved in 30 ml of acetonitrile, cooled to 0° C., added with 0.73 g (3.80 mmol) of 4-toluene sulfonyl chloride, and stirred overnight at room temperature. The reaction was monitored by TLC (PE/

EA=1:1). After the reaction was completed, water was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (1.2 g) as a yellow solid. Yield: 95.65%.

Synthesis of Intermediate 31

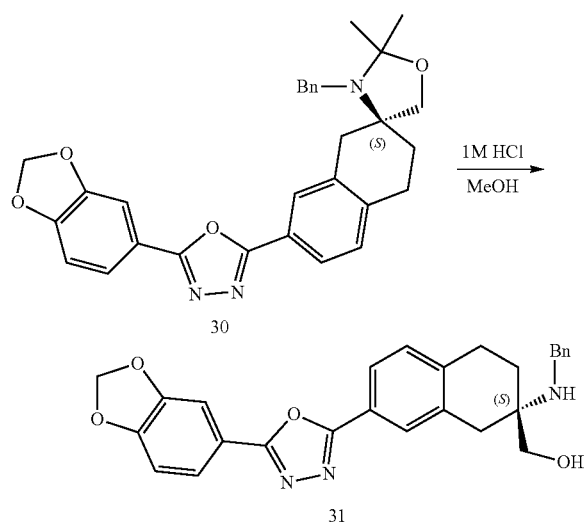

1.2 g (2.42 mmol) of intermediate 30 was dissolved in 5.2 ml of hydrochloric acid (1 M) and 30 ml of methanol, and reacted for 30 min at 80° C. The reaction was monitored by TLC (PE/EA=1:1+Et$_3$N). After the reaction was completed, the resulting mixture was concentrated by rotary evaporation, added with 30 ml of saturated sodium bicarbonate solution and 30 ml of dichloromethane, and separated into layers. The aqueous phase was extracted with dichloromethane. The organic phases were combined, dried and rotary evaporated to dryness to give a crude product, which was purified with silica gel column (eluent: petroleum ether/ethyl acetate=1/1+1% Et$_3$N, v/v) to give a product (0.7 g) as a yellow solid. Yield: 63.64%.

Example 2 (S)-(2-amino-7-(5-(3-fluoro-4-isopropoxyphenyl)-1,3,4-oxadiazol-2-yl)-1,2,3,4-tetrahydronaphthalen-2-yl)methanol

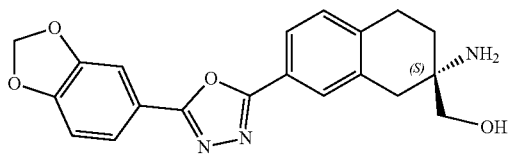

0.7 g (1.54 mmol) of intermediate 31 was dissolved in 30 ml of methanol, added with 4 drops of concentrated hydrochloric acid, purged with nitrogen to remove air, followed by the addition of 0.14 g (20% m/m) of palladium 10% on carbon, purged with hydrogen, and reacted for 5 h at 95° C. The reaction was monitored by TLC (DCM:MeOH=10:1). After the reaction was completed, the resulting mixture was filtered, and the filter cake was washed with plenty of methanol. The filtrate was concentrated by rotary evaporation, added with 30 ml of saturated sodium bicarbonate solution and 30 ml of ethyl acetate, stirred, allowed to stand and separated into layers. The aqueous phase was extracted with ethyl acetate. The organic phases were combined, dried, filtered and rotary evaporated to give a crude product, which was purified with silica gel column (eluent: DCM:MeOH=10/1, V/V) to give the target compound of Example 2 as a faint yellow solid (0.514 g). Yield: 91.35%. LC-MS: 366 [M+1]$^+$, t$_R$=2.64 min. A corresponding hydrogenchloride salt was obtained by mixing the solid with a solution of hydrogen chloride in methanol under stirring. $^1$H NMR (400 MHz, DMSO) δ 8.31 (s, 3H), 7.89 (d, J=6.8 Hz, 2H), 7.77-7.68 (m, 1H), 7.63 (d, J=1.6 Hz, 1H), 7.37 (d, J=8.6 Hz, 1H), 7.15 (d, J=8.1 Hz, 1H), 6.18 (s, 2H), 3.17 (s, 2H), 3.08 (s, 2H), 3.02-2.81 (m, 3H), 2.11-1.90 (m, 2H).

Preparation Example 3

Synthesis of Intermediate 35

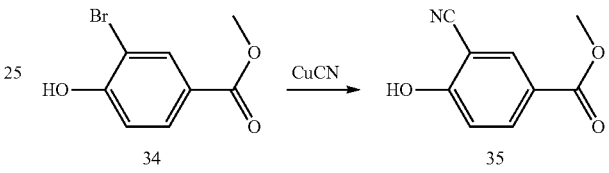

Under the protection of nitrogen, 5.5 g (23.8 mmol) of intermediate 34 and 2.3 g (26.1 mmol) of cuprous cyanide were suspended in 30 ml of N-methylpyrrolidone, and reacted at 200° C. for 5 h. The reaction was monitored by TLC. After the reaction was completed, the resulting mixture was added with 60 ml of water and 60 ml of ethyl acetate, stirred for 30 min, and filtered. The filter cake was washed with ethyl acetate and the mother liquor was extracted with ethyl acetate. The organic phases were combined, dried and rotary evaporated to dryness to give a crude product, which was purified with silica gel column (eluent: ethyl acetate/petroleum ether=1/1, v/v) to give a product (3.6 g) as a yellow oily substance. Yield: 85.3%. LC-MS: 178 [M+1]$^+$, t$_R$=3.251 min.

Synthesis of Intermediate 36

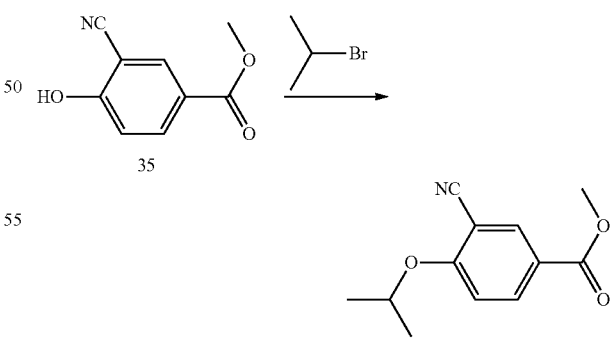

3.6 g (20.3 mmol) of intermediate 35, 9.9 g (81.3 mmol) of 2-bromopropane and 11.2 g (81.3 mmol) of potassium carbonate were suspended in 36 ml of N,N-dimethylformamide, and reacted at 90° C. for 2 h. The reaction was monitored by TLC. After the reaction was completed, the resulting mixture was added with 30 ml of water and 30 ml of ethyl acetate, and separated into layers. The organic phase was washed with water for 3 times, dried and rotary evaporated to dryness to give a crude product (2.6 g) as a yellow oily substance. Yield: 58.1%.

Synthesis of Intermediate 37

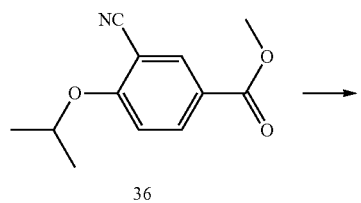

Under the protection of nitrogen, 2.6 g (11.8 mmol) of intermediate 36 was dissolved in 5.9 g (110 mmol, 85%) of hydrazine hydrate, and reacted at 60° C. for 1 h. The reaction was monitored by TLC. After the reaction was completed, the resulting mixture was cooled to room temperature, filtered, washed with water, and pumped to dryness to give a white solid (2 g). Yield: 77.1%.

Synthesis of Intermediate 38

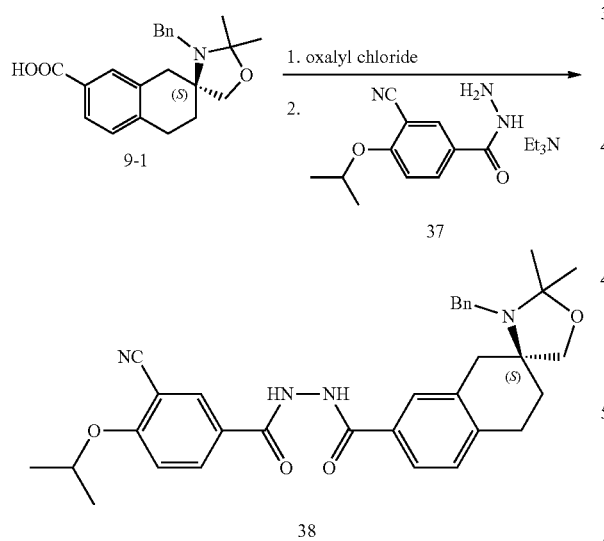

2.6 g (7.6 mmol) of intermediate 9-1 was dissolved in 120 ml of dichloromethane, added with 0.01 g (cat.) of N,N-dimethylformamide and cooled to 0° C. 2.9 g (22.8 mmol) of oxalyl chloride was added dropwise to the mixture, then naturally warmed to room temperature and reacted for 3 h. The reaction was monitored by TLC. After the reaction was completed, the reaction solution was concentrated and added with 50 ml of dichloromethane, as a stock solution. 2 g (9.1 mmol) of compound 37 and 7.9 g (22.8 mmol) of triethylamine were dissolved in 50 ml of dichloromethane and cooled to 0° C. The solution of acyl chloride in dichloromethane obtained above was added dropwise to the mixture, then naturally warmed to room temperature and reacted overnight. The reaction was monitored by TLC. After the reaction was completed, 100 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (4.1 g) as a yellow solid. Yield: 97.3%.

Synthesis of Intermediate 39

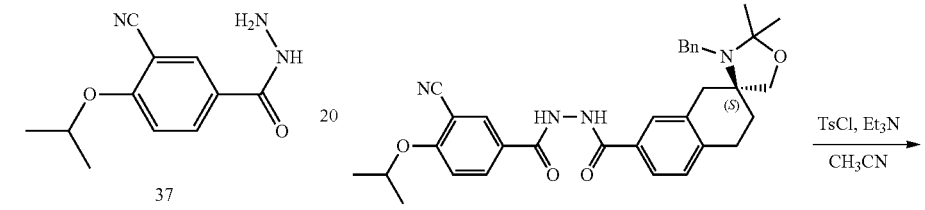

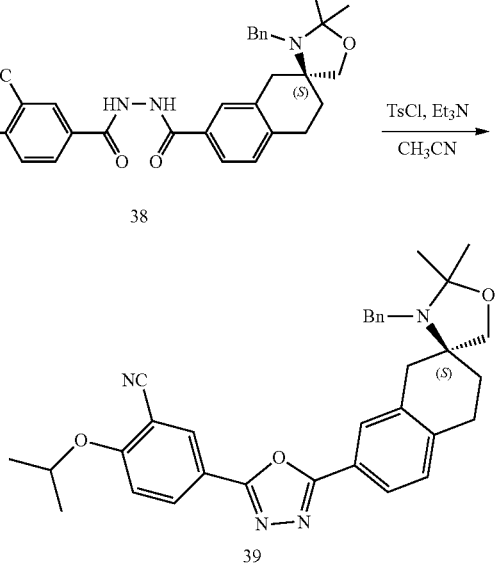

4.1 g (7.4 mmol) of intermediate 38 and 2.2 g (22.2 mmol) of triethylamine were dissolved in 120 ml of acetonitrile, added with 2.1 g (11.1 mmol) of 4-toluene sulfonyl chloride, and stirred overnight at room temperature. The reaction was monitored by TLC. After the reaction was completed, water was added and the resulting mixture was separated into layers. The aqueous phase was extracted with dichloromethane. The organic phases were combined, dried and evaporated to dryness to give a crude product (4.3 g) as a tan solid. Yield: 100%.

Synthesis of Intermediate 40

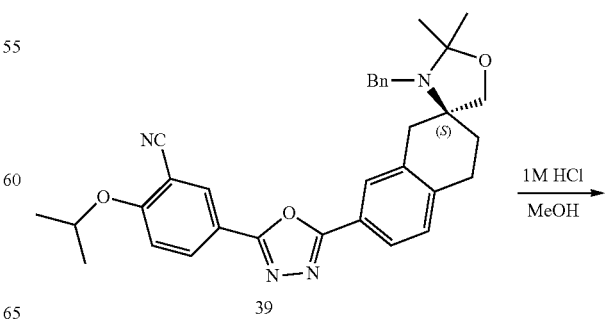

-continued

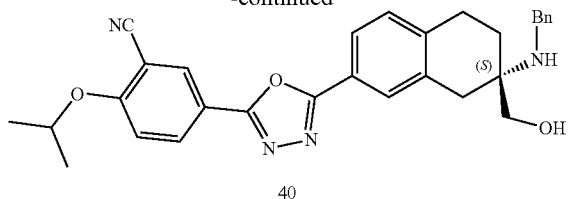

40

4.3 g (8 mmol) of intermediate 39 was dissolved in 20.1 ml of hydrochloric acid (1 M) and 120 ml of methanol, and reacted for 2 h at 80° C. The reaction was monitored by TLC. After the reaction was completed, 50 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (1.5 g) as a white solid. Yield: 37.5%.

Example 3 (S)-5-(5-(7-amino-7-(hydroxymethyl)-5,6,7,8-tetrahydronaphthalen-2-yl)-1,3,4-oxadiazol-2-yl)-2-isopropoxybenzonitrile

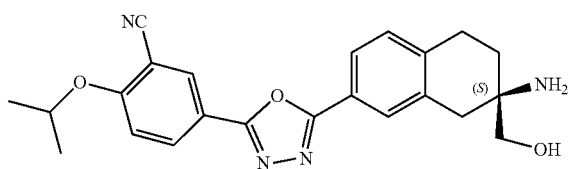

1.5 g (3.0 mmol) of intermediate 40 was dissolved in 45 ml of methanol, added with 0.5 ml of concentrated hydrochloric acid, purged with nitrogen to remove air, followed by the addition of 0.3 g (20% m/m) of palladium 10% on carbon, purged with hydrogen, and reacted for 8 h at 80° C. The reaction was monitored by TLC. After the reaction was completed, the resulting mixture was filtered, and the filter cake was washed with hot methanol. The filtrate was rotary evaporated to dryness to give a crude product (1.5 g), which was recrystallized in 15 ml of methanol, filtered and washed to give the target compound of Example 3 as a white solid (0.65 g). Yield: 54.1%. LC-MS: 405 [M+1]$^+$, $t_R$=3.002 min. A corresponding hydrogenchloride salt was obtained by mixing the solid with a solution of hydrogen chloride in methanol under stirring. $^1$H NMR (400 MHz, DMSO) δ 8.51 (d, J=2.2 Hz, 1H), 8.37 (dd, J=9.0, 2.2 Hz, 1H), 8.12 (s, 3H), 7.96 (d, J=6.6 Hz, 2H), 7.54 (d, J=9.2 Hz, 1H), 7.40 (d, J=8.6 Hz, 1H), 5.62 (t, J=5.1 Hz, 1H), 5.01-4.87 (m, 1H), 3.47 (d, J=4.9 Hz, 2H), 3.22-2.83 (m, 5H), 2.06-1.89 (m, 2H), 1.38 (d, J=6.0 Hz, 6H).

Example 4 (S)-5-(5-(7-amino-7-(hydroxymethyl)-5,6,7,8-tetrahydronaphthalen-2-yl)-1,3,4-oxadiazol-2-yl)-2-isopropoxybenzamide

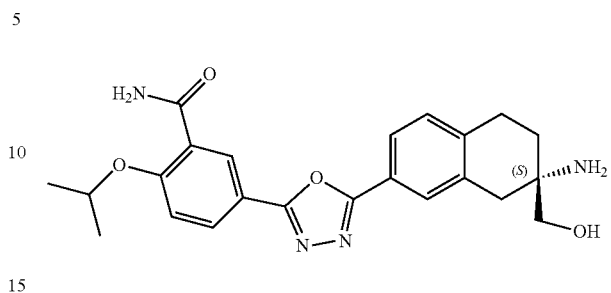

0.2 g (0.49 mmol) of the target compound of Example 3 was dissolved in 5 ml of dimethyl sulfoxide, added with 0.25 g (1.8 mmol) of potassium carbonate, cooled to 0° C., added dropwise with 2 ml of hydrogen peroxide solution (30%), and stirred for 2 h at room temperature. The reaction was monitored by TLC. After the reaction was completed, the resulting solution was added with 30 ml of water, stirred for 10 min, filtered, washed with water, and pumped to dryness to give a crude product. The crude product was recrystallized in 20 ml of methanol, filtered and washed to give the target compound of Example 4 as a white solid (110 mg). Yield: 53.4%. A corresponding hydrogenchloride salt was obtained by mixing the solid with a solution of hydrogen chloride in methanol under stirring. H NMR (400 MHz, DMSO) δ 8.50 (d, J=2.3 Hz, 1H), 8.26 (s, 3H), 8.19 (dd, J=8.8, 2.3 Hz, 1H), 7.90 (s, 2H), 7.79 (s, 1H), 7.65 (s, 1H), 7.40 (t, J=9.5 Hz, 2H), 6.11-5.14 (br s, 1H), 5.01-4.85 (m, 1H), 3.48 (s, 3H), 3.19-2.76 (m, 4H), 2.00 (t, J=6.4 Hz, 2H), 1.40 (d, J=6.0 Hz, 6H).

Example 5 (S)-5-(5-(7-amino-7-(hydroxymethyl)-5,6,7,8-tetrahydronaphthalen-2-yl)-1,3,4-oxadiazol-2-yl)-2-hydroxybenzonitrile

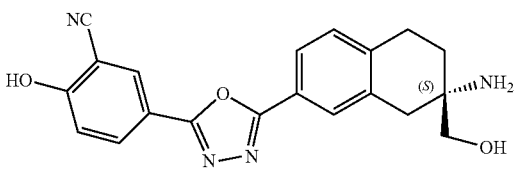

100 mg (0.24 mmol) of the target compound of Example 3 was dissolved in sulphuric acid (50%), and reacted for 1 h at 90° C. The reaction was monitored by TLC. After the reaction was completed, the resulting mixture was added with saturated sodium bicarbonate solution to adjust pH to 2-3, filtered, washed with water, and pumped to dryness to give the target compound of Example 5 as a white solid (35 mg). Yield: 34.3%. LC-MS: 363 [M+1]$^+$, $t_R$=1.142 min. A corresponding hydrogenchloride salt was obtained by mixing the solid with a solution of hydrogen chloride in methanol under stirring.

Preparation Example 4

Synthesis of Intermediate 46

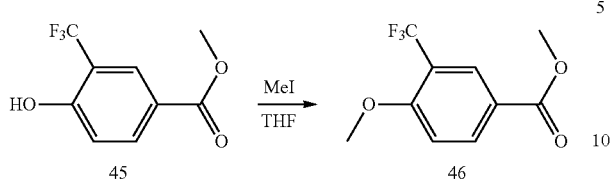

2.0 g (9.08 mmol) of material 45, 0.98 g (18.17 mmol) of sodium methoxide and a small amount of TBAB were suspended in 40 ml of THF, stirred for 30 min at room temperature, followed by the addition of 1.7 ml of methyl iodide, stirred and reacted at room temperature. The reaction was monitored by TLC (PE/EA=3:1). The reaction solution was added with methyl iodide until the material was reacted completely, then concentrated by rotary evaporation, added with 40 ml of saturated sodium bicarbonate solution and 40 ml of dichloromethane, stirred, allowed to stand and separated. The aqueous phase was extracted with 2×40 ml of dichloromethane. The organic phases were combined, dried and rotary evaporated to dryness to give a crude product (2.1 g) as a yellow solid. Yield: 100%. LC-MS: 235 [M+1]$^+$, $t_R$=4.457 min.

Synthesis of Intermediate 47

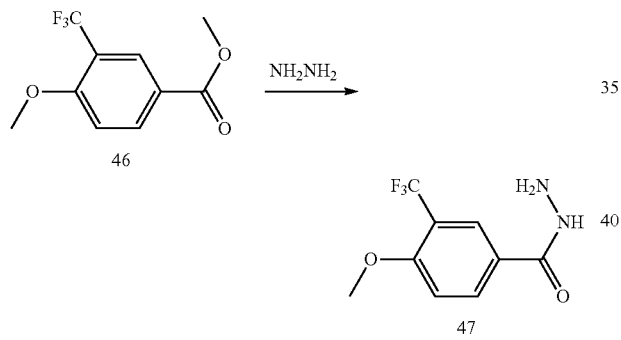

Under the protection of nitrogen, 2.12 g (9.08 mmol) of intermediate 46 was suspended in 6.4 ml (108.96 mmol, 85%) of hydrazine hydrate, and reacted at 85° C. for 100 min. The reaction was monitored by TLC (PE/EA=1:1+ Et$_3$N). After the reaction was completed, the resulting mixture was cooled to room temperature, filtered, washed with water, and pumped to dryness to give a crude product (1.96 g), as a white solid. Yield: 92.4%. LC-MS: 235 [M+1]$^+$, $t_R$=3.005 min.

Synthesis of Intermediate 48

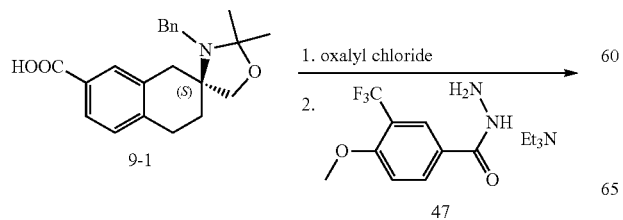

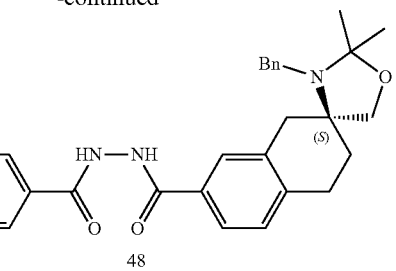

2.9 g (8.25 mmol) of intermediate 9-1 was dissolved in 60 ml of dichloromethane, added with 0.01 g (cat.) of N,N-dimethylformamide and cooled to 0° C. 2.1 ml (24.75 mmol) of oxalyl chloride was added dropwise to the mixture, then naturally warmed to room temperature and reacted for 1 h. After the reaction was completed, the reaction solution was concentrated and added with 30 ml of dichloromethane, as a stock solution. 2.32 g (9.9 mmol) of compound 47 and 3.5 ml (24.75 mmol) of triethylamine were dissolved in 30 ml of dichloromethane and cooled to 0° C. The solution of acyl chloride in dichloromethane obtained above was added dropwise to the mixture, then naturally warmed to room temperature and reacted for 3 h. The reaction was monitored by TLC (PE/EA=1:1+AcOH). After the reaction was completed, 70 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (3.1 g) as a brown solid. Yield: 66.2%. LC-MS: 568 [M+1], $t_R$=4.678 min.

Synthesis of Intermediate 49

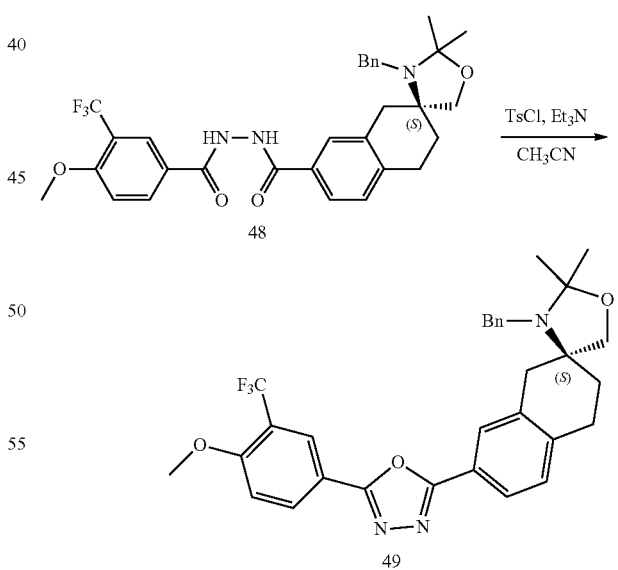

3.1 g (5.46 mmol) of intermediate 48 and 2.3 ml (16.38 mmol) of triethylamine were dissolved in 124 ml of acetonitrile, cooled to 0° C., added with 1.56 g (8.19 mmol) of 4-toluene sulfonyl chloride, and stirred overnight at room temperature. The reaction was monitored by TLC (PE/EA=1:1). After the reaction was completed, water was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=3/1, v/v) to give a product (1.9 g) as a faint yellow solid. Yield: 63.3%. LC-MS: 550 [M+1]⁺, $t_R$=6.464 min.

Synthesis of Intermediate 50

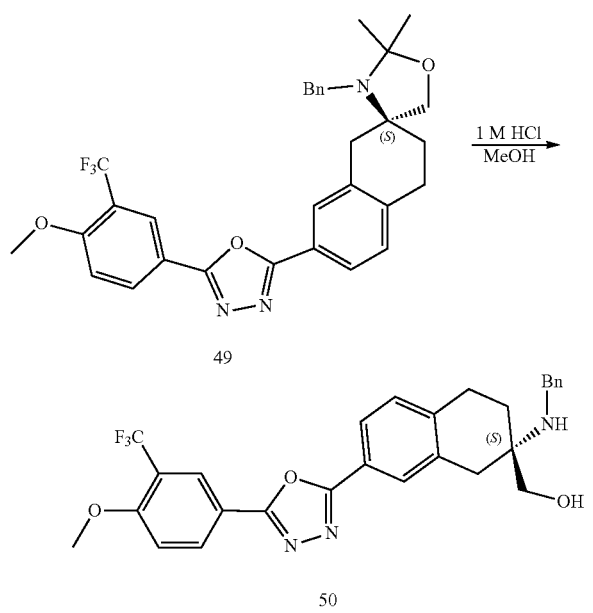

1.0 g (1.82 mmol) of intermediate 49 was dissolved in 4.55 ml of hydrochloric acid (1 M) and 30 ml of methanol, and reacted for 100 min at 80° C. The reaction was monitored by TLC (PE/EA=1:1+Et₃N). After the reaction was completed, the resulting mixture was concentrated by rotary evaporation, added with 50 ml of saturated sodium bicarbonate solution and 50 ml of dichloromethane, and separated into layers. The aqueous phase was extracted with dichloromethane. The organic phases were combined, dried and rotary evaporated to dryness to give a crude product, which was purified with silica gel column (eluent: petroleum ether/ethyl acetate=1/2+1% Et₃N, v/v) to give a product (0.8 g) as a white solid. Yield: 86.32%.

Example 6 (S)-(2-amino-7-(5-(4-methoxy-3-(trifluoromethyl)phenyl)-1,3,4-oxadiazol-2-yl)-1,2,3,4-tetrahydronaphthalen-2-yl)methanol

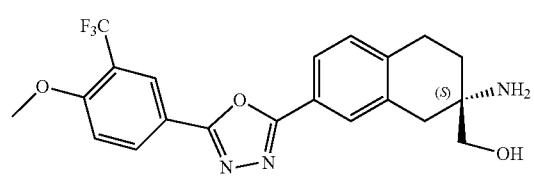

0.8 g (1.57 mmol) of intermediate 50 was dissolved in 16 ml of methanol, added with 0.1 ml of concentrated hydrochloric acid, purged with nitrogen to remove air, followed by the addition of 0.16 g (20% m/m) of palladium 10% on carbon, purged with hydrogen, and reacted for 5 h at 95° C. The reaction was monitored by TLC (DCM:MeOH=10:1). After the reaction was completed, the resulting mixture was filtered, and the filter cake was washed with hot methanol. The filtrate was rotary evaporated to dryness to give a crude product, which was recrystallized in 24 ml of methanol, filtered and washed to give the target compound of Example 6 as a white solid (0.36 g). Yield: 54.67%. LC-MS: 420 [M+1]⁺, $t_R$=3.002 min. A corresponding hydrogenchloride salt was obtained by mixing the solid with a solution of hydrogen chloride in methanol under stirring.

Preparation Example 5

Synthesis of Intermediate 54

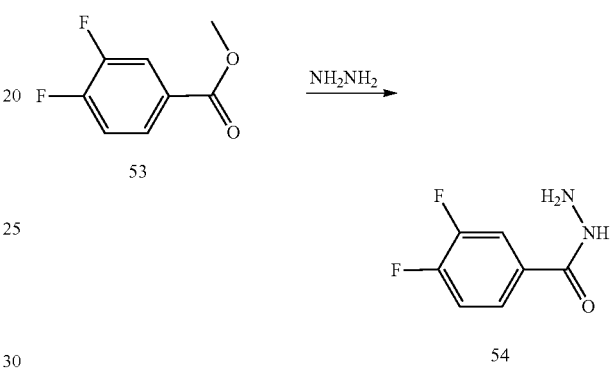

Under the protection of nitrogen, 2.0 g (11.62 mmol) of material 53 was dissolved in 20 ml of methanol, added with 8.2 ml (139.44 mmol, 85%) of hydrazine hydrate, and reacted at room temperature for 1.5 h. The reaction was monitored by TLC (PE/EA=3:1). After the reaction was completed, the resulting mixture was added with 50 ml of water and stirred to precipitate out a solid, filtered, washed with water, and pumped to dryness. The aqueous phase was extracted with EA. The organic phase was dried, concentrated by rotary evaporation, and pumped to dryness to give a product (2 g), as a white solid. Yield: 100%. LC-MS: 173 [M+1]⁺, $t_R$=2.528 min.

Synthesis of Intermediate 56

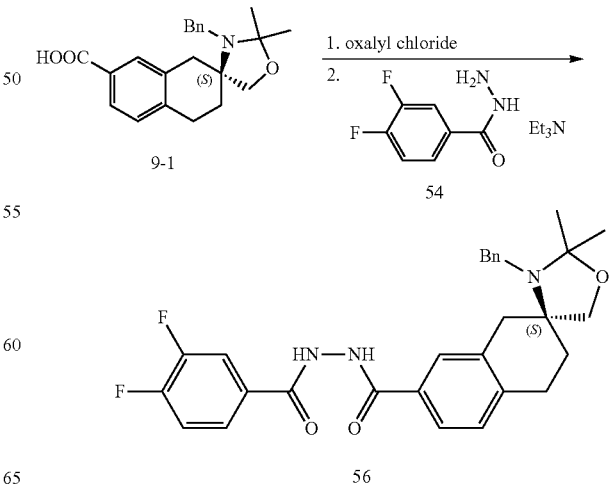

1 g (2.84 mmol) of intermediate 9-1 was dissolved in 40 ml of dichloromethane, added with 0.01 g (cat.) of N,N-dimethylformamide and cooled to 0° C. 0.72 ml (8.52 mmol) of oxalyl chloride was added dropwise to the mixture, then naturally warmed to room temperature and reacted for 1 hour. After the reaction was completed, the reaction solution was concentrated and added with 20 ml of dichloromethane, as a stock solution. 0.54 g (3.13 mmol) of compound 54 and 1.2 ml (8.52 mmol) of triethylamine were dissolved in 20 ml of dichloromethane and cooled to 0° C. The solution of acyl chloride in dichloromethane obtained above was added dropwise to the mixture, then naturally warmed to room temperature and reacted overnight. The reaction was monitored by TLC (PE/EA=3:1+AcOH). After the reaction was completed, 40 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (0.7 g) as a yellow solid. Yield: 48.8%. LC-MS: 506 [M+1]$^+$, $t_R$=4.587 min.

Synthesis of Intermediate 57

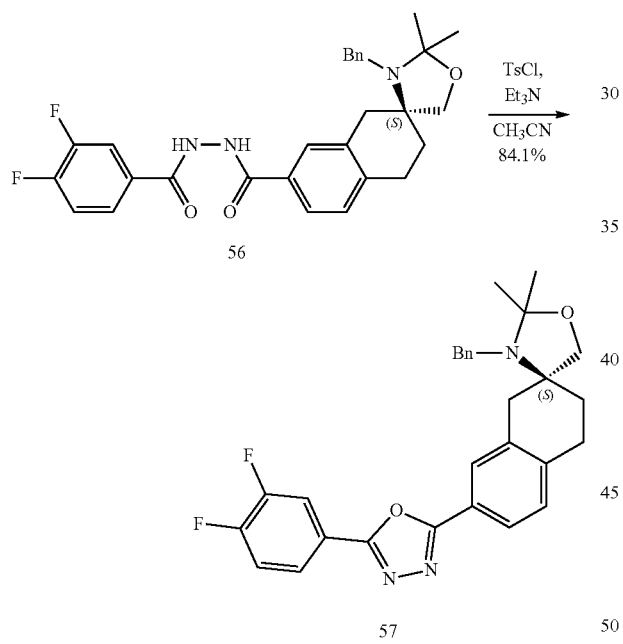

0.7 g (1.38 mmol) of intermediate 56 and 0.6 ml (4.14 mmol) of triethylamine were dissolved in 38 ml of acetonitrile, cooled to 0° C., added with 0.32 g (1.66 mmol) of 4-toluene sulfonyl chloride, and stirred for 5 h at room temperature. The reaction was monitored by TLC (PE/EA=1:1). After the reaction was completed, water was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=10/1, v/v) to give a product (0.43 g) as a white solid. Yield: 63.9%. LC-MS: 488[M+1]$^+$, $t_R$=6.464 min.

Synthesis of Intermediate 58

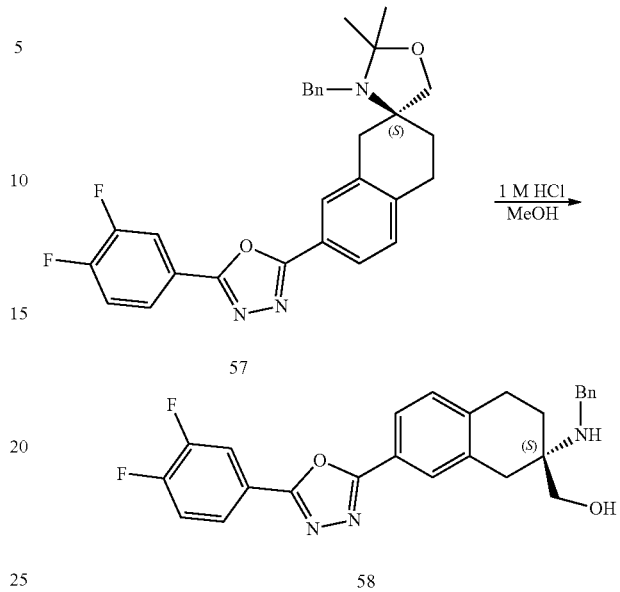

0.4 g (0.82 mmol) of intermediate 57 was dissolved in 2.1 ml of hydrochloric acid (1 M) and 16 ml of methanol, and reacted for 1 h at 80° C. The reaction was monitored by TLC (PE/EA=1:1+Et$_3$N). After the reaction was completed, 40 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1+1% Et$_3$N, v/v) to give a product (0.242 g) as a white solid. Yield: 66.0%.

Example 7 (S)-(2-amino-7-(5-(3,4-difluorophenyl)-1,3,4-oxadiazol-2-yl)-1,2,3,4-tetrahydronaphthalen-2-yl)methanol

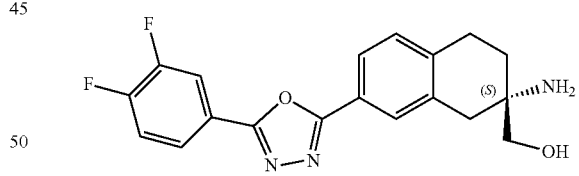

0.24 g (0.54 mmol) of intermediate 58 was dissolved in 8 ml of methanol, added with 0.01 ml of concentrated hydrochloric acid, purged with nitrogen to remove air, followed by the addition of 0.048 g of palladium 10% on carbon, purged with hydrogen, and reacted for 5 h at 95° C. The reaction was monitored by TLC (DCM:MeOH=10:1). After the reaction was completed, the resulting mixture was filtered, and the filter cake was washed with hot methanol. The filtrate was rotary evaporated to dryness to give a crude product (1.5 g), which was purified with silica gel column (eluent: dichloromethane/methanol=10/1) to give the target compound of Example 7 as a white solid (0.18 g). Yield: 93.3%. LC-MS: 358 [M+1]$^+$, $t_R$=3.717 min. A corresponding hydrogenchloride salt was obtained by mixing the solid with a solution of hydrogen chloride in methanol under stirring. $^1$H NMR (400 MHz, DMSO) δ 8.30-8.16 (m, 1H), 8.09-7.96 (m, 1H), 7.87 (d, J=6.7 Hz, 2H), 7.79-7.64 (m, 1H), 7.34 (d, J=8.4 Hz, 1H), 5.38-4.14 (br, 3H), 3.74-3.16 (m, 5H), 3.05-2.65 (m, 4H), 1.91-1.60 (m, 2H).

Preparation Example 6

Synthesis of Intermediate 62

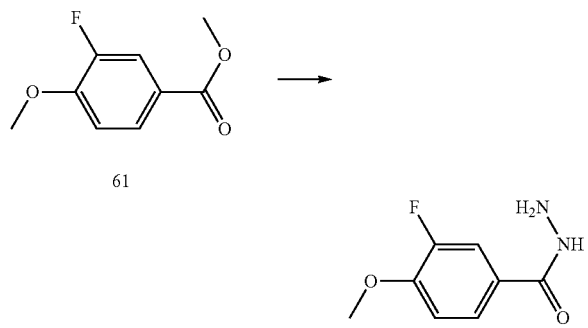

Under the protection of nitrogen, 0.928 g (5.04 mmol) of intermediate 61 was dissolved in 3.56 g (60.48 mmol, 85%) of hydrazine hydrate, and reacted at 85° C. for 2 h. The reaction was monitored by TLC. After the reaction was completed, the resulting mixture was cooled to room temperature, filtered, and pumped to dryness to give a white solid (0.369 g). Yield: 39.68%.

Synthesis of Intermediate 63

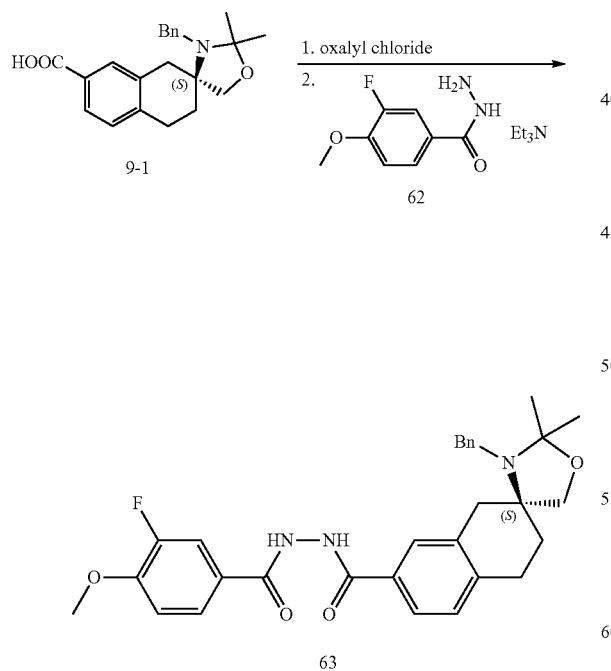

0.47 g (1.34 mmol) of intermediate 9-1 was dissolved in 20 ml of dichloromethane, added with 3 drops of N,N-dimethylformamide and cooled to 0° C. 0.34 ml (4 mmol) of oxalyl chloride was added dropwise to the mixture, then naturally warmed to room temperature and reacted for 1 h. After the reaction was completed, the reaction solution was concentrated and added with 20 ml of dichloromethane, as a stock solution. 0.369 g (2 mmol) compound 62 and 0.56 ml (4 mmol) of triethylamine were dissolved in 20 ml of dichloromethane and cooled to 0° C. The solution of acyl chloride in dichloromethane obtained above was added dropwise to the mixture, then naturally warmed to room temperature and reacted overnight. The reaction was monitored by TLC (PE/EA=3:1+AcOH). After the reaction was completed, 30 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (0.302 g) as a yellow solid. Yield: 43.28%. LC-MS: 518 [M+1]$^+$, $t_R$=5.462 min.

Synthesis of Intermediate 64

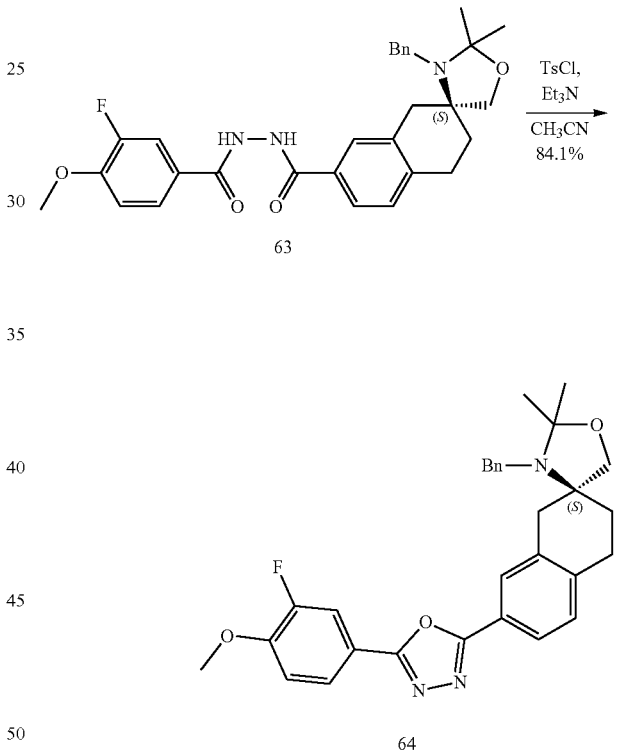

0.302 g (0.58 mmol) of intermediate 63 and 0.24 ml (1.74 mmol) of triethylamine were dissolved in 10 ml of acetonitrile, cooled to 0° C., added with 0.166 g (0.87 mmol) of 4-toluene sulfonyl chloride, and stirred overnight at room temperature. The reaction was monitored by TLC (PE/EA=1:1). After the reaction was completed, water was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=1/1, v/v) to give a product (0.332 g) as a yellow solid. Yield: 100%.

Synthesis of Intermediate 65

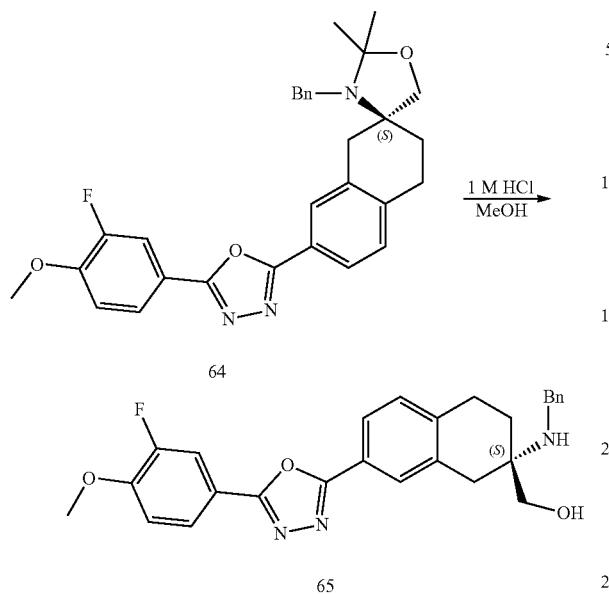

0.332 g (0.58 mmol) of intermediate 64 was dissolved in 1.25 ml of hydrochloric acid (1 M) and 10 ml of methanol, and reacted for 30 min at 80° C. The reaction was monitored by TLC (PE/EA=1:1+Et₃N). After the reaction was completed, the resulting mixture was concentrated by rotary evaporation, added with 10 ml of saturated sodium bicarbonate solution and 10 ml of dichloromethane, and separated into layers. The aqueous phase was extracted with dichloromethane. The organic phases were combined, dried and rotary evaporated to dryness to give a crude product, which was purified with silica gel column (eluent: petroleum ether/ethyl acetate=1/1+1% Et₃N, v/v) to give a product (0.214 g) as a yellow solid. Yield: 81.03%.

Example 8 (S)-(2-amino-7-(5-(3-fluoro-4-methoxyphenyl)-1,3,4-oxadiazol-2-yl)-1,2,3,4-tetrahydronaphthalen-2-yl)methanol

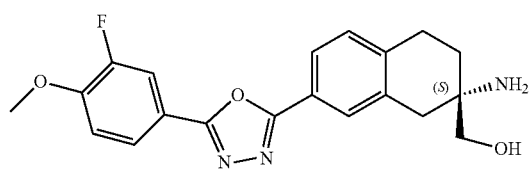

0.214 g (0.47 mmol) of intermediate 65 was dissolved in 10 ml of methanol, added with 2 drops of concentrated hydrochloric acid, purged with nitrogen to remove air, followed by the addition of 0.04 g (20% m/m) of palladium 10% on carbon, purged with hydrogen, and reacted for 4 h at 95° C. The reaction was monitored by TLC (DCM:MeOH=10:1). After the reaction was completed, the resulting mixture was filtered, and the filter cake was washed with plenty of methanol. The filtrate was concentrated by rotary evaporation, added with 10 ml of saturated sodium bicarbonate solution and 10 ml of ethyl acetate, stirred, allowed to stand and separated into layers. The aqueous phase was extracted with ethyl acetate. The organic phases were combined, dried, filtered and rotary evaporated to give a crude product, which was purified with silica gel column (eluent: DCM:MeOH=10/1, V/V) to give the target compound of Example 8 as a faint yellow solid (0.138 g). Yield: 79.49%. LC-MS: 370 [M+1]⁺, $t_R$=1.334 min. A corresponding hydrogenchloride salt was obtained by mixing the solid with a solution of hydrogen chloride in methanol under stirring.

Preparation Example 7

Synthesis of Intermediate 69

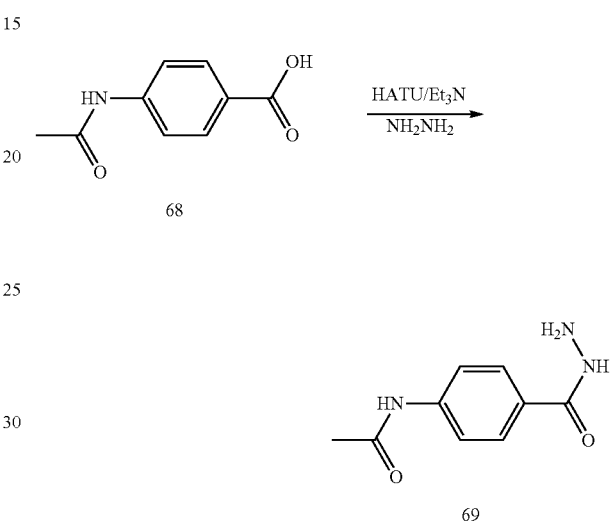

1.0 g (5.6 mmol) of intermediate 68 was dissolved in 10 ml of N,N-dimethylformamide, added with 2.34 ml (16.8 mmol) of triethylamine, cooled to 0° C., then added with 2.51 g (6.16 mmol) of N,N,N',N'-tetramethyl-o-(7-azabenzotriazol-1-yl)uronium hexafluorophosphate, and stirred for 30 min. The resulting solution was added dropwise to a solution of 2.8 g (56 mmol) of hydrazine hydrate in 10 ml of N,N-dimethylformamide and reacted overnight. The reaction was monitored by TLC. After the reaction was completed, the reaction solution was rotary evaporated to dryness, added with 10 ml of saturated sodium bicarbonate solution and 10 ml of dichloromethane, and separated into layers. The aqueous phase was extracted with dichloromethane. The organic phases were combined, dried and rotary evaporated to dryness to give a crude product, which was purified with silica gel column (eluent: DCM/MeOH=10/1, v/v) to give a product (0.24 g) as a white solid. Yield: 22.18%. LC-MS: 194 [M+1]⁺, $t_R$=1.435 min.

Synthesis of Intermediate 70

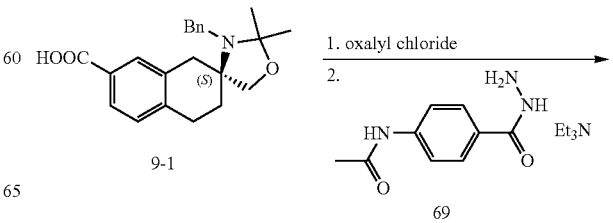

-continued

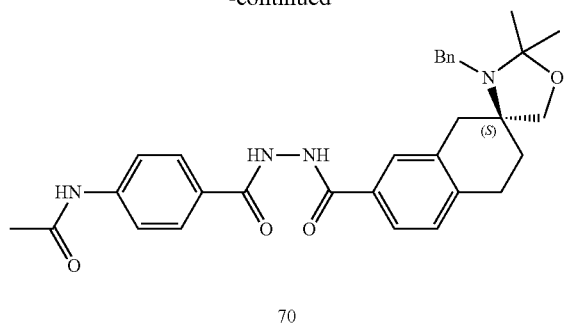

70

2.1 g (5.97 mmol) of intermediate 9-1 was dissolved in 80 ml of dichloromethane, added with 10 drops of N,N-dimethylformamide and cooled to 0° C. 1.52 ml (17.92 mmol) of oxalyl chloride was added dropwise to the mixture, then naturally warmed to room temperature and reacted for 1 h. After the reaction was completed, the reaction solution was concentrated and added with 80 ml of dichloromethane, as a stock solution. 1.732 g (8.96 mmol) compound 69 and 2.5 ml (17.92 mmol) of triethylamine were dissolved in 80 ml of dichloromethane and cooled to 0° C. The solution of acyl chloride in dichloromethane obtained above was added dropwise to the mixture, then naturally warmed to room temperature and reacted overnight. The reaction was monitored by TLC (PE/EA=3:1+AcOH). After the reaction was completed, 120 ml of saturated sodium bicarbonate solution was added and the resulting mixture was separated into layers. The aqueous phase was extracted with dichloromethane. The organic phases were combined, dried and evaporated to dryness to give a crude product, which was purified with silica gel column (eluent: petroleum ether/ethyl acetate=1/1, v/v) to give a product (2.0 g) as a yellow solid. Yield: 63.16%. LC-MS: 527 [M+1]$^+$, $t_R$=2.457 min.

Synthesis of Intermediate 71

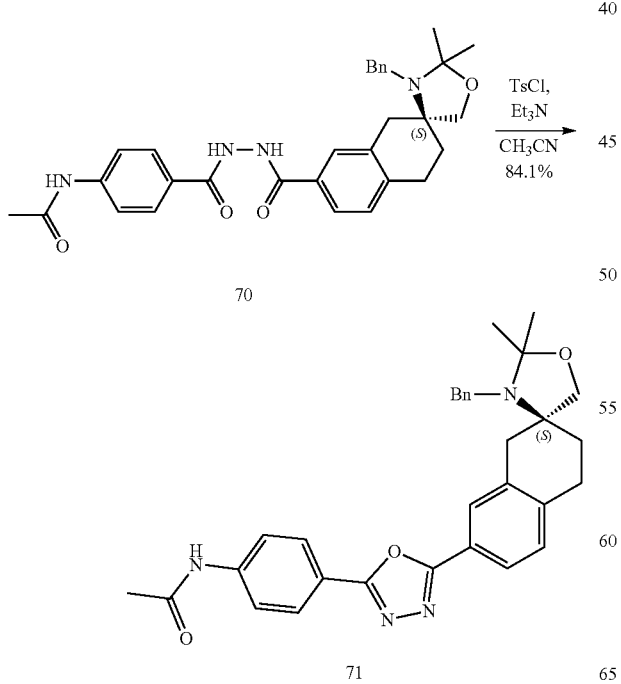

2.0 g (3.8 mmol) of intermediate 70 and 1.59 ml (11.4 mmol) of triethylamine were dissolved in 50 ml of acetonitrile, cooled to 0° C., added with 1.087 g (5.7 mmol) of 4-toluene sulfonyl chloride, and stirred overnight at room temperature. The reaction was monitored by TLC (PE/EA=1:1). After the reaction was completed, water was added to the resulting mixture, which was separated into layers. The aqueous phase was extracted with dichloromethane. The organic phases were combined, dried and evaporated to dryness to give a crude product, which was purified with silica gel column (eluent: petroleum ether/ethyl acetate=5/1, v/v) to give a product (2.2 g) as a yellow solid. Yield: 100%.

Synthesis of Intermediate 72

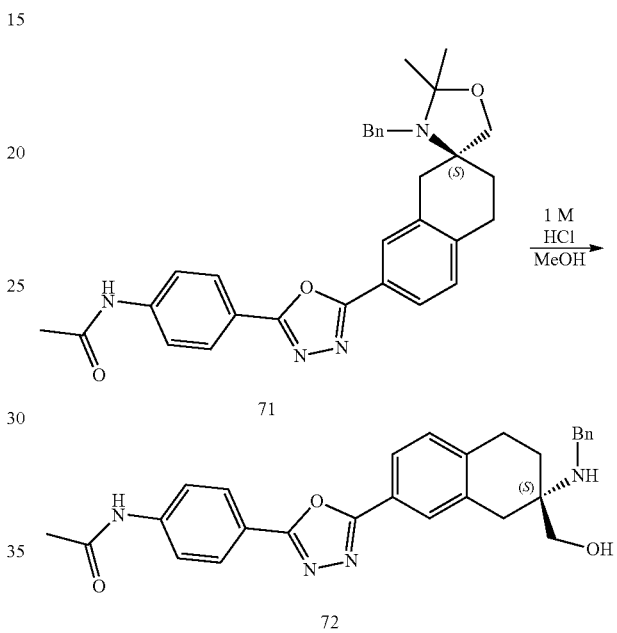

2.2 g (3.8 mmol) of intermediate 71 was dissolved in 8.17 ml of hydrochloric acid (1 M) and 50 ml of methanol, and reacted for 30 min at 80° C. The reaction was monitored by TLC (PE/EA=1:1+Et$_3$N). After the reaction was completed, the resulting mixture was concentrated by rotary evaporation, added with 50 ml of saturated sodium bicarbonate solution and 50 ml of dichloromethane, and separated into layers. The aqueous phase was extracted with dichloromethane. The organic phases were combined, dried and evaporated to dryness to give a crude product, which was purified with silica gel column (eluent: petroleum ether/ethyl acetate=1/1+1% Et$_3$N, v/v) to give a product (0.8 g) as a yellow solid. Yield: 45.0%.

Example 9 (S)—N-(4-(5-(7-amino-7-(hydroxymethyl)-5,6,7,8-tetrahydronaphthalen-2-yl)-1,3,4-oxadiazol-2-yl)phenyl)acetamide

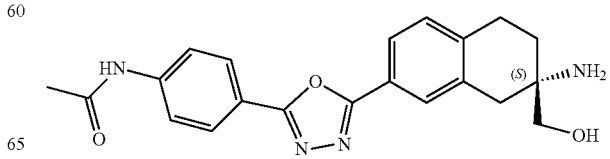

0.8 g (1.71 mmol) of intermediate 72 was dissolved in 30 ml of methanol, added with 5 drops of concentrated hydrochloric acid, purged with nitrogen to remove air, followed by the addition of 0.16 g (20% m/m) of palladium 10% on carbon, purged with hydrogen, and reacted for 4 h at 95° C. The reaction was monitored by TLC (DCM:MeOH=10:1). After the reaction was completed, the resulting mixture was filtered, and the filter cake was washed with plenty of methanol. The filtrate was concentrated by rotary evaporation, added with 30 ml of saturated sodium bicarbonate solution and 30 ml of ethyl acetate, stirred, allowed to stand and separated into layers. The aqueous phase was extracted with ethyl acetate. The organic phases were combined, dried, filtered and rotary evaporated to give a crude product, which was purified with silica gel column (eluent: DCM:MeOH=10/1, V/V) to give the target compound of Example 9 as a faint yellow solid (0.326 g). Yield: 50.38%. LC-MS: 379 [M+1]$^+$, $t_R$=1.103 min. A corresponding hydrogenchloride salt was obtained by mixing the solid with a solution of hydrogen chloride in methanol under stirring.

Preparation Example 8

Synthesis of Intermediate 76

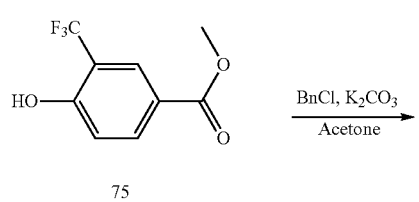

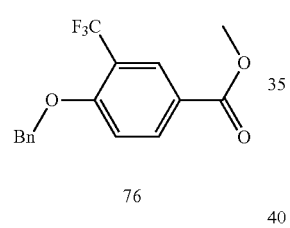

1.0 g (4.54 mmol) of material 75, 1.9 g (13.62 mmol) of potassium carbonate and 2.6 ml (27.00 mmol) of benzyl chloride were suspended in 40 ml of acetone, heated at reflux and reacted overnight. The reaction was monitored by TLC (PE/EA=3:1). After the material 75 was reacted completely, the reaction solution was concentrated by rotary evaporation, added with 40 ml of saturated sodium bicarbonate solution and 40 ml of dichloromethane, stirred, allowed to stand and separated into layers. The aqueous phase was extracted with 40 ml of dichloromethane. The organic phases were combined, dried and rotary evaporated to dryness to give a crude product, which was purified with silica gel column (eluent: petroleum ether/ethyl acetate=20/1, v/v) to give a product (1.4 g) as a white solid. Yield: 100%.

Synthesis of Intermediate 77

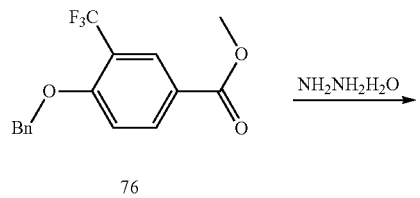

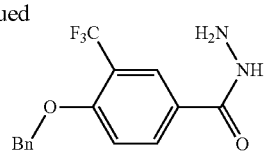

Under the protection of nitrogen, 1.4 g (4.54 mmol) of intermediate 76 was suspended in 40 ml of methanol and 6.4 ml (108.96 mmol, 85%) of hydrazine hydrate, and reacted at 85° C. for 180 min. The reaction was monitored by TLC (PE/EA=1:1+Et$_3$N). After the reaction was completed, the resulting mixture was concentrated by rotary evaporation, cooled to room temperature, added with 20 ml of water and stirred to precipitate out a solid, filtered, washed with water, and pumped to dryness to give a product (1.4 g), as a white solid. Yield: 100%. LC-MS: 311 [M+1]$^+$, $t_R$=1.799 min.

Synthesis of Intermediate 78

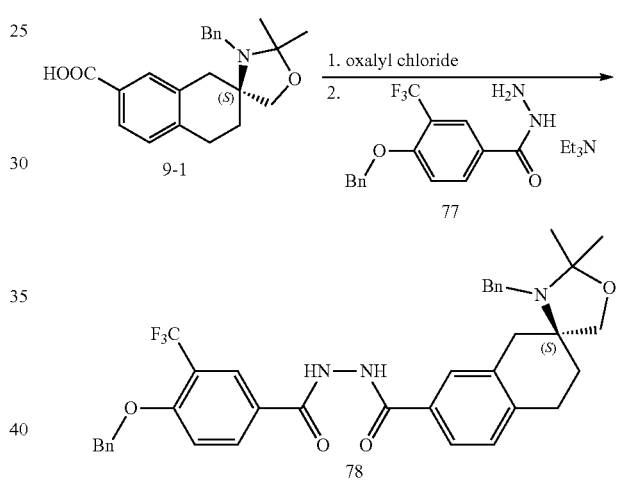

1.36 g (3.87 mmol) of intermediate 9-1 was dissolved in 27 ml of dichloromethane, added with 0.01 g (cat.) of N,N-dimethylformamide and cooled to 0° C. 1.0 ml (11.61 mmol) of oxalyl chloride was added dropwise to the mixture, then naturally warmed to room temperature and reacted for 1 h. After the reaction was completed, the reaction solution was concentrated and added with 30 ml of dichloromethane, as a stock solution. 1.2 g (3.87 mmol) of intermediate 77 and 1.62 ml (11.61 mmol) of triethylamine were dissolved in 30 ml of dichloromethane and cooled to 0° C. The solution of acyl chloride in dichloromethane obtained above was added dropwise to the mixture, then naturally warmed to room temperature and reacted overnight. The reaction was monitored by TLC (PE/EA=3:1+AcOH). After the reaction was completed, 60 ml of saturated sodium bicarbonate solution was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=2/1, v/v) to give a product (1.4 g) as a yellow solid. Yield: 56.2%. LC-MS: 644 [M+1]$^+$, $t_R$=2.396 min.

Synthesis of Intermediate 79

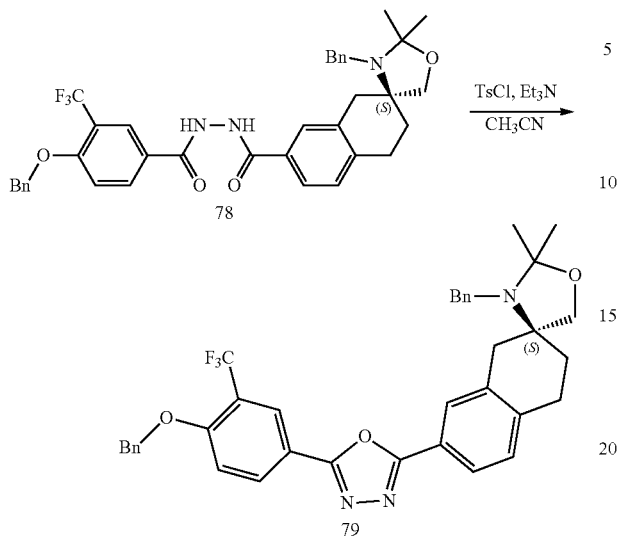

1.4 g (2.17 mmol) of intermediate 78 and 1.0 ml (6.51 mmol) of triethylamine were dissolved in 56 ml of acetonitrile, cooled to 0° C., added with 0.5 g (2.61 mmol) of 4-toluene sulfonyl chloride, and stirred overnight at room temperature. The reaction was monitored by TLC (PE/EA=1:1). After the reaction was completed, water was added to the resulting mixture, which was separated into layers. The aqueous phase was extracted with dichloromethane. The organic phases were combined, dried and rotary evaporated to dryness to give a crude product, which was purified with silica gel column (eluent: petroleum ether/ethyl acetate=3/1, v/v) to give a product (0.6 g) as a faint yellow solid. Yield: 44.2%.

Synthesis of Intermediate 80

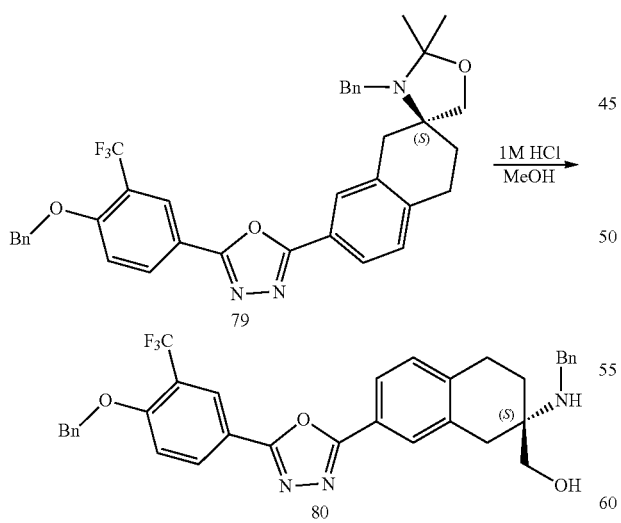

0.6 g (0.95 mmol) of intermediate 79 was dissolved in 2.4 ml of hydrochloric acid (1 M) and 30 ml of methanol, and reacted for 120 min at 80° C. to precipitate out a solid. The reaction was monitored by TLC (PE/EA=1:1+Et₃N). After the reaction was completed, the resulting mixture was filtrated under vacuum. The mother liquor was concentrated by rotary evaporation, added with 30 ml of saturated sodium bicarbonate solution and 30 ml of dichloromethane, and separated into layers. The aqueous phase was extracted with dichloromethane. The organic phases were combined, dried and rotary evaporated to dryness to give a crude product, which was purified with silica gel column (eluent: petroleum ether/ethyl acetate=1/2+1% Et₃N, v/v) to give a product (0.426 g) as a white solid. Yield: 76.57%.

Example 10 (S)-4-(5-(7-amino-7-(hydroxymethyl)-5,6,7,8-tetrahydronaphthalen-2-yl)-1,3,4-oxadiazol-2-yl)-2-(trifluoromethyl)phenol

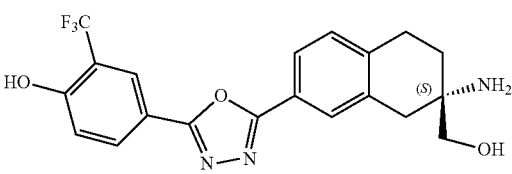

0.426 g (0.727 mmol) of intermediate 80 was dissolved in 16 ml of methanol, added with 0.01 ml of concentrated hydrochloric acid, purged with nitrogen to remove air, followed by the addition of 0.09 g of palladium 10% on carbon, purged with hydrogen, and reacted overnight at 95° C. The reaction was monitored by TLC (DCM:MeOH=10:1). After the reaction was completed, the resulting mixture was filtered, and the filter cake was washed with hot methanol. The filtrate was concentrated by rotary evaporation, added with 1% sodium hydrate solution to adjust pH to 9-10. The aqueous phase was extracted with dichloromethane, added with hydrochloric acid (1 M) to adjust pH 5.8-6.2 to precipitate out a white solid, stirred for 30 min at room temperature, and then filtered under vacuum to give the target compound of Example 10 (25 mg) as a white solid, which is prone to oxidative degradation and stored at low temperature under the protection of nitrogen. Yield: 8.5%. LC-MS: 406 [M+1]⁺, $t_R$=1.328 min. A corresponding hydrogenchloride salt was obtained by mixing the solid with a solution of hydrogen chloride in methanol under stirring.

Preparation Example 9

Synthesis of Intermediate 84

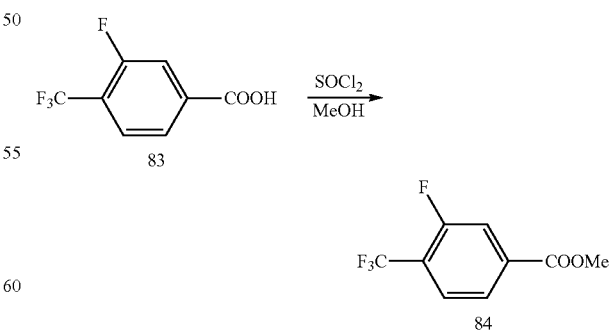

1.0 ml (14.4 mmol) of thionyl chloride was added to 20 ml of methanol at low temperature, stirred and reacted for 1 h in an ice-water bath, followed by the addition of 1.0 g of material 83 to the reaction vessel, naturally warmed, then heated to 55° C., stirred and reacted for 1 h. The reaction was monitored by TLC (PE/EA=3:1+AcOH). After the material 83 was reacted completely, the reaction solution was concentrated by rotary evaporation, added with 20 ml of saturated sodium bicarbonate solution and 20 ml of ethyl acetate, stirred, allowed to stand and separated into layers. The aqueous phase was extracted with 40 ml of ethyl acetate twice. The organic phases were combined, dried and rotary evaporated to dryness to give a crude product (0.7 g), as an oily substance. Yield: 65.7%.

Synthesis of Intermediate 85

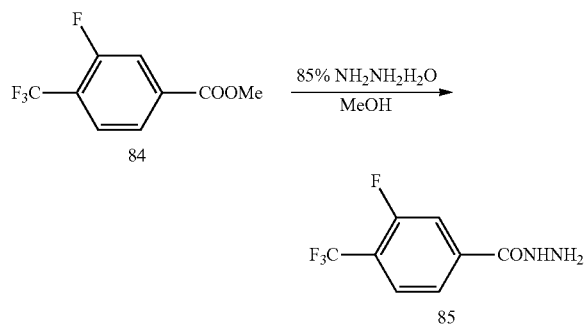

Under the protection of nitrogen, 0.7 g (3.2 mmol) of intermediate 84 was suspended in 7 ml of methanol and 1.9 ml (32 mmol, 85%) of hydrazine hydrate, and reacted at room temperature overnight. The reaction was monitored by TLC (PE/EA=3:1). After the reaction was completed, the resulting mixture was added with 20 ml of water and 20 ml of DCM, stirred, separated and extracted with DCM twice. The organic phases were combined, dried, filtered, concentrated under reduced pressure and pumped to dryness to give a white solid (0.7 g). Yield: 100%. LC-MS: 223 [M+1]$^+$, $t_R$=1.879 min.

Synthesis of Intermediate 86

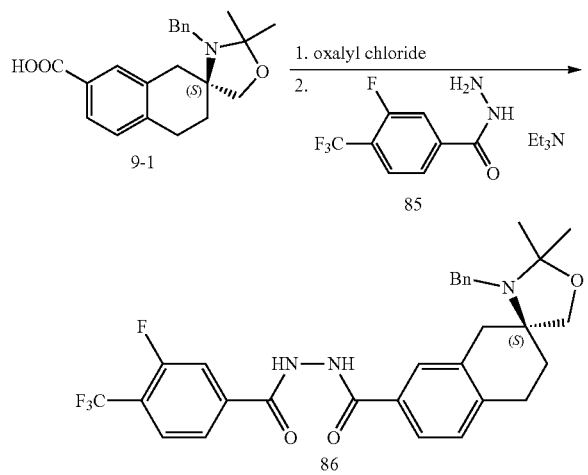

1.0 g (3.1 mmol) of intermediate 9-1 was dissolved in 40 ml of dichloromethane, added with 0.01 g (cat.) of N,N-dimethylformamide and cooled to 0° C. 0.8 ml (9.3 mmol) of oxalyl chloride was added dropwise to the mixture, then naturally warmed to room temperature and reacted for 1 h. After the reaction was completed, the reaction solution was concentrated and added with 20 ml of dichloromethane, as a stock solution. 0.7 g (3.87 mmol) intermediate 85 and 1.3 ml (9.3 mmol) of triethylamine were dissolved in 20 ml of dichloromethane and cooled to 0° C. The solution of acyl chloride in dichloromethane obtained above was added dropwise to the mixture, then naturally warmed to room temperature and reacted overnight. The reaction was monitored by TLC (PE/EA=3:1+AcOH). After the reaction was completed, 40 ml of saturated sodium bicarbonate solution was added and the resulting mixture was separated into layers. The aqueous phase was extracted with dichloromethane. The organic phases were combined, dried and rotary evaporated to dryness to give a crude product (1.5 g). Yield: 87.1%.

Synthesis of Intermediate 87

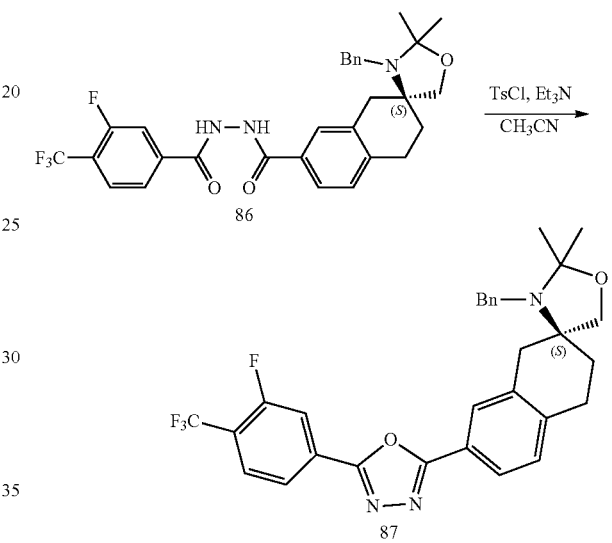

1.5 g (3.1 mmol) of intermediate 86 and 1.3 ml (9.3 mmol) of triethylamine were dissolved in 60 ml of acetonitrile, cooled to 0° C., added with 0.88 g (4.65 mmol) of 4-toluene sulfonyl chloride, and stirred overnight at room temperature. The reaction was monitored by TLC (PE/EA=1:1). After the reaction was completed, water was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=3/1, v/v) to give a product (1.3 g) as a faint yellow solid. Yield: 78.0%. LC-MS: 538 [M+1]$^+$, $t_R$=3.251 min.

Synthesis of Intermediate 88

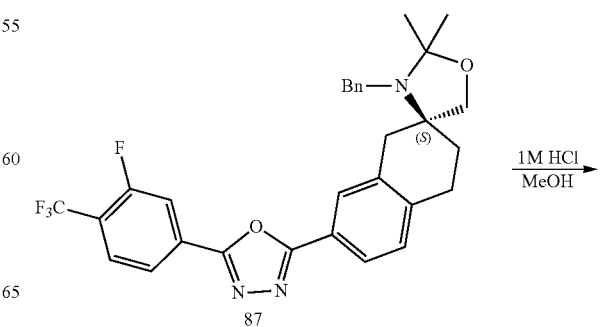

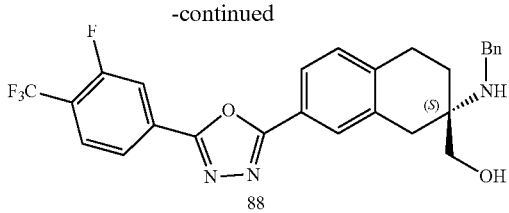

1.3 g (2.4 mmol) of intermediate 87 was dissolved in 6 ml of hydrochloric acid (1 M) and 40 ml of methanol, and reacted for 3 h at 80° C. The reaction was monitored by TLC (PE/EA=1:1+Et$_3$N). After the reaction was completed, the resulting mixture was concentrated under reduced pressure, added with sodium hydrate solution (10%) and saturated sodium bicarbonate solution to adjust pH about 8, and extracted with dichloromethane. The organic phases were combined, dried and rotary evaporated to dryness to give a crude product, which was purified with silica gel column (eluent: petroleum ether/ethyl acetate=1/1+1% Et$_3$N, v/v) to give a product (0.6 g) as a white solid. Yield: 50.2%.

Example 11 (S)-(2-amino-7-(5-(3-fluoro-4-(trifluoromethyl)phenyl)-1,3,4-oxadiazol-2-yl)-1,2,3,4-tetrahydronaphthalen-2-yl)methanol

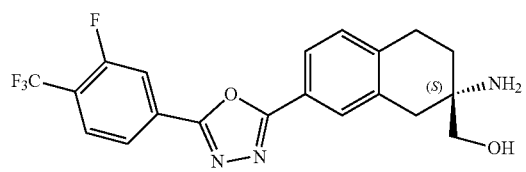

0.6 g (1.2 mmol) of intermediate 88 was dissolved in 20 ml of methanol, added with 0.01 ml of concentrated hydrochloric acid, purged with nitrogen to remove air, followed by the addition of 0.12 g (20% m/m) of 10% wet palladium on carbon, purged with hydrogen, and reacted for 6 h at 85° C. The reaction was monitored by TLC (DCM:MeOH=10:1). After the reaction was completed, the resulting mixture was filtered while hot, and the filter cake was washed with hot methanol. The filtrate was concentrated by rotary evaporation, added with 6 ml of methanol and a solution (1 ml, 10%) of hydrogen chloride in methanol, warmed to reflux, stirred for 30 min, then naturally cooled to room temperature, and filtered under vacuum to give a white solid (0.1 g). The filtrate was rotary evaporated to dryness and the processes above-mentioned were repeated to give a white solid (0.076 g). The two white solids obtained were combined to give the target compound of Example 11 (0.176 g, hydrogenchloride salt). Yield: 33.0%. LC-MS: 408 [M+1]$^+$, t$_R$=1.936 min.

Preparation Example 10

Synthesis of Intermediate 92

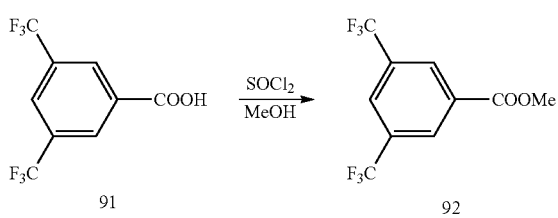 [SMILES: "MeOH" ; O=C(O)c1cc(C(F)(F)F)cc(C(F)(F)F)c1 ; "SOCl2" ; COC(=O)c1cc(C(F)(F)F)cc(C(F)(F)F)c1]

1.7 ml (23.1 mmol) of thionyl chloride was added to 40 ml of methanol at low temperature, stirred and reacted for 1 h in an ice-water bath, followed by the addition of 2.0 g of material 91, naturally warmed, then heated to 80° C., stirred and reacted for 1 h. The reaction was monitored by TLC (PE/EA=3:1+AcOH). After the material 91 was reacted completely, the reaction solution was concentrated by rotary evaporation, added with 20 ml of saturated sodium bicarbonate solution and 20 ml of ethyl acetate, stirred, allowed to stand and separated into layers. The aqueous phase was extracted with 40 ml of ethyl acetate twice. The organic phases were combined, dried and rotary evaporated to dryness to give a crude product (1.5 g), as an oily substance. Yield: 71.6%.

Synthesis of Intermediate 93

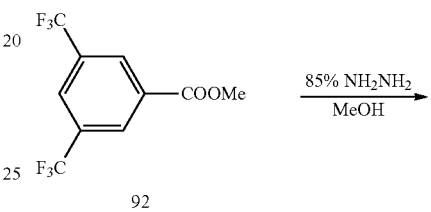

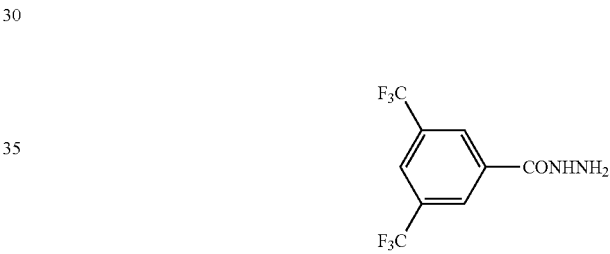

Under the protection of nitrogen, 1.5 g (5.5 mmol) of intermediate 92 was suspended in 30 ml of methanol and 3.2 ml (55 mmol, 85%) of hydrazine hydrate, and reacted at room temperature overnight. The reaction was monitored by TLC (PE/EA=3:1). After the reaction was completed, the resulting mixture was added with 20 ml of water and 20 ml of DCM, stirred, separated and extracted with DCM twice. The organic phases were combined, dried, filtered, concentrated under reduced pressure and pumped to dryness to give a white solid (1.5 g). Yield: 100%. LC-MS: 273 [M+1]$^+$, t$_R$=2.034 min.

Synthesis of Intermediate 94

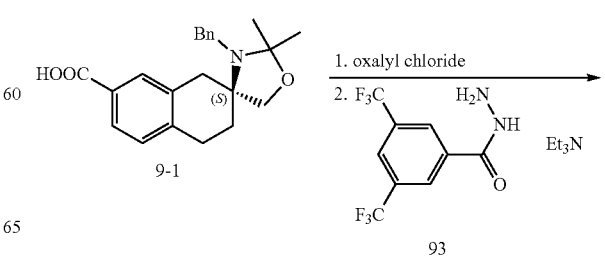

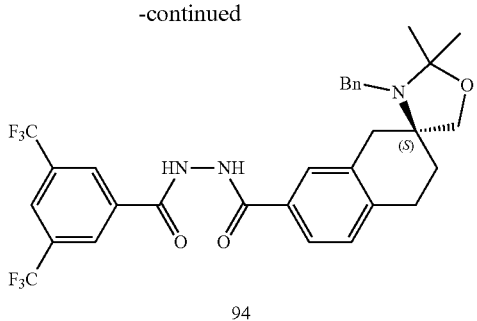

94

1.7 g (5 mmol) of intermediate 9-1 was dissolved in 68 ml of dichloromethane, added with 0.02 g (cat.) of N,N-dimethylformamide and cooled to 0° C. 1.3 ml (15 mmol) of oxalyl chloride was added dropwise to the mixture, then naturally warmed to room temperature and reacted for 1 hour. After the reaction was completed, the reaction solution was concentrated and added with 34 ml of dichloromethane, as a stock solution. 1.5 g (5.5 mmol) intermediate 93 and 2.1 ml (15 mmol) of triethylamine were dissolved in 40 ml of dichloromethane and cooled to 0° C. The solution of acyl chloride in dichloromethane obtained above was added dropwise to the mixture, then naturally warmed to room temperature and reacted overnight. The reaction was monitored by TLC (PE/EA=3:1+AcOH). After the reaction was completed, 40 ml of saturated sodium bicarbonate solution was added and the resulting mixture was separated into layers. The aqueous phase was extracted with dichloromethane. The organic phases were combined, dried and rotary evaporated to dryness to give a crude product (3.0 g). Yield: 100%.

Synthesis of Intermediate 95

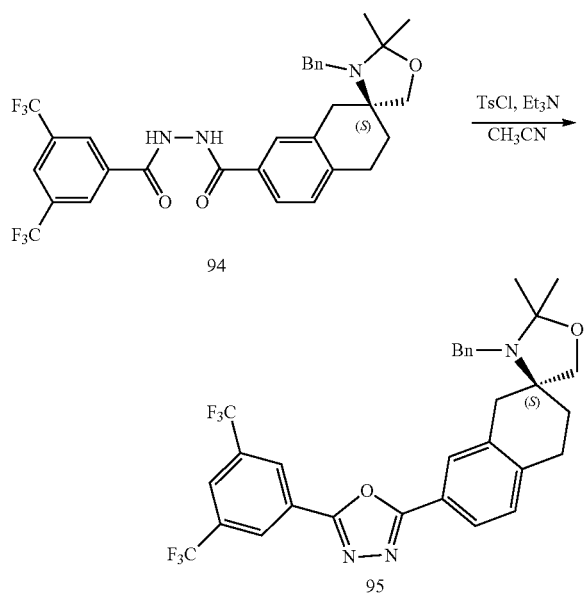

3.0 g (5 mmol) of crude intermediate 94 and 2.1 ml (15 mmol) of triethylamine were dissolved in 120 ml of acetonitrile, cooled to 0° C., added with 1.1 g (6 mmol) of 4-toluene sulfonyl chloride, and stirred overnight at room temperature. The reaction was monitored by TLC (PE/EA=1:1). After the reaction was completed, water was added and the resulting mixture was separated into layers. The aqueous phase was extracted with dichloromethane. The organic phases were combined, dried and rotary evaporated to dryness to give a crude product, which was purified with silica gel column (eluent: petroleum ether/ethyl acetate=10/1, v/v) to give a product (1.3 g) as a bubble-shaped solid. Yield: 44.2%. LC-MS: 588.5 [M+1]$^+$, $t_R$=3.300 min.

Synthesis of Intermediate 96

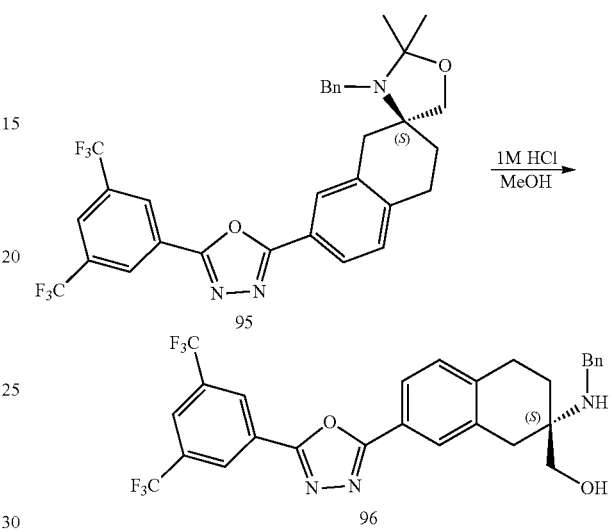

1.3 g (2.2 mmol) of intermediate 95 was dissolved in 5.5 ml of hydrochloric acid (1 M) and 50 ml of methanol, and reacted for 2 h at 90° C. The reaction was monitored by TLC (PE/EA=1:1+Et$_3$N). After the reaction was completed, the resulting mixture was concentrated under reduced pressure, added with sodium hydrate solution (10%) and saturated sodium bicarbonate solution to adjust pH about 8, and extracted with dichloromethane. The organic phases were combined, dried and rotary evaporated to dryness to give a crude product, which was purified with silica gel column (eluent: petroleum ether/ethyl acetate=1/1+1% Et$_3$N, v/v) to give a product (0.6 g) as a white solid. Yield: 49.8%.

Example 12 (S)-(2-amino-7-(5-(3,5-bis(trifluoromethyl)phenyl)-1,3,4-oxadiazol-2-yl)-1,2,3,4-tetrahydronaphthalen-2-yl)methanol

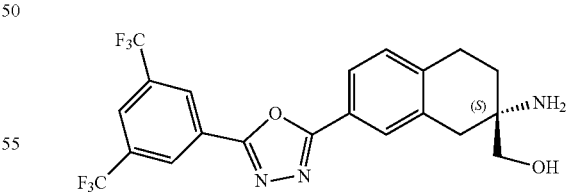

0.6 g (1.1 mmol) of intermediate 96 was dissolved in 34 ml of methanol, added with 0.01 ml of concentrated hydrochloric acid, purged with nitrogen to remove air, followed by the addition of 0.12 g (20% m/m) of 10% wet palladium on carbon, purged with hydrogen, and reacted for 6 h at 90° C. The reaction was monitored by TLC (DCM:MeOH=10:1). After the reaction was completed, the resulting mixture was filtered while hot, and the filter cake was washed with hot methanol. The filtrate was concentrated by rotary evaporation to give a crude product as a white solid. The crude product was purified with silica gel column (eluent: dichloromethane/methanol=5/1, v/v), then dissolved in 20 ml of DCM (containing a small amount of methanol) and 20 ml of water, stirred and separated. The aqueous phase was extracted with DCM. The DCM phases were combined, dried, and filtered. The filtrate was added with an appropriate amount of solution of hydrogen chloride in methanol, rotary evaporated to dryness, and pumped to dryness under reduced pressure to give the target compound of Example 12 (0.126 g, hydrogenchloride salt). Yield: 33%. Purity: 96.1%. LC-MS: 458 [M+1]$^+$, $t_R$=1.961 min.

Example 13 (S)-(2-amino-7-(5-(3,4-diethoxyphenyl)-1,3,4-oxadiazol-2-yl)-1,2,3,4-tetrahydronaphthalen-2-yl)methanol

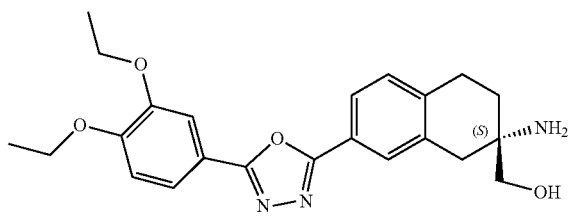

The chiral compound of the present example was obtained by using the chiral intermediate 7-1 as a starting material in a manner similar to the preparation method of example 20 in WO2013181840. LC-MS: 410.2 [M+1]$^+$, $t_R$=1.757 min. H NMR (400 MHz, DMSO) δ 7.90-7.77 (m, 2H), 7.68 (dd, J=8.4, 1.9 Hz, 1H), 7.59 (d, J=1.9 Hz, 1H), 7.33 (d, J=7.9 Hz, 1H), 7.17 (d, J=8.5 Hz, 1H), 4.98 (br s, 1H), 4.14 (p, J=6.8 Hz, 5H), 3.29 (s, 2H), 3.04-2.60 (m, 5H), 1.88-1.59 (m, 2H), 1.43-1.30 (m, 6H). A hydrogenchloride salt was obtained by processing the chiral compound with a small amount of solution of hydrogen chloride in methanol.

Example 14 (S)-(2-amino-7-(5-(4-isopropoxy-3-(trifluoromethyl)phenyl)-1,3,4-oxadiazol-2-yl)-1,2,3,4-tetrahydronaphthalen-2-yl)methanol

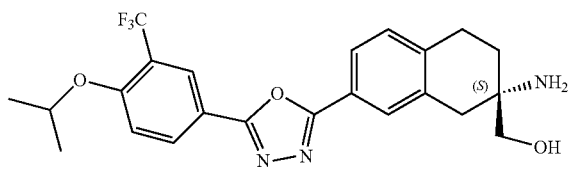

The chiral compound of the present example was obtained by using the chiral intermediate 7-1 as a starting material in a manner similar to the preparation method of example 11 in WO2013181840. A hydrogenchloride salt was obtained by processing the chiral compound with a small amount of solution of hydrogen chloride in methanol. LC-MS: 448.5 [M+1]$^+$, $t_R$=3.183 min. H NMR (400 MHz, DMSO) δ 8.43-8.31 (m, 1H), 8.27 (s, 1H), 8.13 (s, 3H), 7.94 (d, J=5.5 Hz, 2H), 7.56 (d, J=9.0 Hz, 1H), 7.40 (d, J=8.6 Hz, 1H), 5.61 (t, J=5.1 Hz, 1H), 5.03-4.87 (m, 1H), 3.47 (d, J=5.0 Hz, 2H), 3.17-2.79 (m, 4H), 2.07-1.86 (m, 2H), 1.35 (d, J=6.0 Hz, 6H).

Biological Activity Assays

The compounds of the invention were detected for biological activity hereinafter:

Example 15 Effects of Amino Alcohol Compounds on the Expression of CD4, CD8 and CD19 on Peripheral Blood Cell in Mice 1. Test Materials:
Mice (C57 BL/6, 8 weeks)
FITC Rat Anti-Mouse CD8a: BD, Cat. #553030.
PE Rat Anti-Mouse CD4: BD, Cat. #557308.
APC Rat Anti-Mouse CD19: BD, Cat. #561738.
The compounds used in the test were prepared by the chemical department of Beijing Forelandpharma Co. Ltd.

2. Test Method:
Routs of administration: intragastric administration, once a day, and continuous administration for four days.

After the administration, supraorbital venous blood was collected from the mouse, added to an EP tube (1.5 ml) containing an anticoagulant, and kept on the ice. The resulting mixture was transferred to a test tube, centrifuged at 4° C. and 1200 rpm/min for 5 min, removed with the supernatant liquid, added with a lysate, processed with cell lysis on the ice for 5 min, then pre-dyed, added with diluted antibody, and incubated away from light for 30 min. After the incubation, the resulting mixture was washed, removed with the supernatant liquid, added with stationary liquid, and kept in a refrigerator at 4° C. away from light for the test of flow cytometry.

3. Test Results

TABLE 1

Effects of Amino Alcohol Compounds on the Expression of CD4, CD8 and CD19 on Peripheral Blood Cell in Mice

| Number | Example | CD4 (%) | | CD8 (%) | | CD19 (%) | |
|---|---|---|---|---|---|---|---|
| | | 1 mg/kg | 5 mg/kg | 1 mg/kg | 5 mg/kg | 1 mg/kg | 5 mg/kg |
| 1 | vehicle | 25.7 | | 14.5 | | 47.5 | |
| 2 | 13 | 23.4 | 11.6 | 12.7 | 9.4 | 56.8 | 53.8 |
| 3 | 1 | 10.9 | 1.2 | 10.0 | 1.8 | 39.0 | 17.5 |
| 4 | 2 | 23.1 | 16.4 | 13.0 | 8.6 | 44.8 | 35.2 |
| 5 | 3 | 22.1 | 7.2 | 11.9 | 6.1 | 39.3 | 24.7 |
| 6 | 6 | 17.8 | 8.7 | 17.0 | 5.7 | 34.0 | 29.1 |
| 7 | 4 | 27.1 | 27.0 | 14.5 | 12.3 | 47.1 | 43.6 |
| 8 | 7 | 26.5 | 13.4 | 14.5 | 9.2 | 45.2 | 40.6 |
| 9 | 8 | 33.4 | 30.0 | 16.6 | 16.0 | 36.8 | 41.7 |
| 10 | 9 | 33.1 | 31.9 | 17.3 | 17.0 | 42.5 | 44.3 |
| 11 | 5 | 31.5 | 27.1 | 16.8 | 14.7 | 44.3 | 43.8 |
| 12 | 10 | 31.1 | 27.7 | 15.3 | 14.0 | 44.3 | 35.7 |
| 13 | 11 | 23.5 | 20.5 | 14.9 | 13.8 | 52.1 | 54.0 |
| 14 | 12 | 15.2 | 2.8 | 9.6 | 3.4 | 53.2 | 38.1 |

Example 16 β-arrestin Testing Experiments (PathHunter β-Arrestin Testing System)

Test Method

1. PathHunter β-arrestin testing system was used to detect the biological activity of the compounds.
2. β-arrestin engineering cells were cultured on 386-well culture plates and placed in an incubator at 37° C.
3. The sample to be tested was diluted with reaction solution in 5-fold dilution.
4. The diluted sample to be tested was added to the engineering cells and the reaction was induced and observed.
5. The chemiluminescence signal produced in the test may be detected by multifunctional enzyme marker (PerkinElmer Envision™).

Test Analysis and Results

6. The data obtained was analyzed using the data analysis software of CBIS (ChemInnovation, CA) to achieve $EC_{50}$, and the test results are shown in Table 2.

TABLE 2

Biological Activity of the Compounds in Example 3 and Example 13
β-arrestin Test
$EC_{50}$ (nM)

| Compound | S1P1 | S1P2 | S1P3 | S1P4 |
|---|---|---|---|---|
| S1P | 25.2 | 26.4 | 26.3 | 189.7 |
| Example 13 | 21.6 | >100,000 | 613 | >100,000 |
| Example 3 | 4.56 | >100,000 | 2114 | >100,000 |

Example 17 Test of Fluorescence Detection (FLIPR Assay)

Test Method and Results

The sample to be tested was dissolved in DMSO and diluted with detection buffer solution in 3-fold dilution. A reagent and a positive control were diluted in the same way.

The reactions of the agonist, the reagent and the positive control were detected by a device of FLIPRTETRA with a total detection time of 180 s to estimate the ability to activate GPCR (S1P5) of each compound. The results are shown in Table 3.

TABLE 3

Biological Activity of the Compounds in Example 3 and Example 13
FLIPR Test
$EC_{50}$ (nM)

| Compound | S1P5 |
|---|---|
| S1P | 23 |
| Example 13 | >10,000 |
| Example 3 | 250 |

Example 18

Test Method

1. HEK293 engineering cells stably expressed with hERG potassium channel were used to test the compounds.

2. Patch Clamp Detection

The cells were separated by TrypLE™ Express before the test. $3 \times 10^3$ of cells were spread on a cover plate, cultured in 24-well plate and tested 18 hours later. The signals produced by voltage stimulation of potassium currents in cells were recorded by electrophysiological techniques.

Data Analysis and Results

First of all, currents after the action of drug of each concentration and blank control were standardized separately $$\left(\frac{\text{Peak tail current compound}}{\text{Peak tail current vehicle}}\right),$$

and then the corresponding inhibition ratio of each concentration was calculated $$\left(1 - \frac{\text{Peak tail current compound}}{\text{Peak tail current vehicle}}\right).$$

The average and the standard error were calculated for each concentration, and 50% inhibiting concentration of each compound was calculated according to the following equation:

$$\text{inhibition} = \frac{1}{1 + \left(\frac{IC50}{C}\right)^h}$$

The dose-dependent effect was obtained through nonlinear fitting with the equation above. C refers to drug concentration, IC50 refers to 50% inhibiting concentration and h refers to hill coefficient. The curve fitting and the calculation of IC50 were processed by IGOR software. The results are shown in Table 4.

TABLE 4

HERG Test of Example 13 and Example 14
hERG Test

| Compound | $IC_{50}$ (µM) |
|---|---|
| Example 13 | 1.2 |
| Example 14 | 0.87 |
| Example 3 | 7.8 |

The embodiments of the present invention have been described above. However, the present invention is not limited to the embodiments above mentioned. Any modification, equivalent substitution and improvement, etc., which are made within the spirit and principle of the invention, should fall within the scope of the invention.

What is claimed is:

1. An amino alcohol derivative represented by the following Formula I', or a pharmaceutically acceptable salt, stereoisomer, isotopic label, solvate, polymorph, or prodrug thereof:

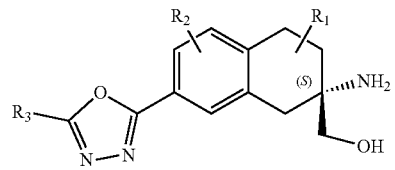

wherein $R_1$ and $R_2$ are the same or different, and is each independently selected from the group consisting of H, —F, —Cl, —Br, —I, —OH, —SH, —CN, —COOH, —$NO_2$ and the following group of $C_{1-40}$ alkyl, $C_{1-40}$ alkoxy, $C_{2-40}$ alkenyl, $C_{2-40}$ alkynyl, $C_{3-20}$ cycloalkyl, $C_{3-20}$ cycloalkoxy, 3- to 20-membered heterocyclyl, 3- to 20-membered heterocycloxy, $C_{6-20}$ aryl, $C_{6-20}$ aryloxy, 5- to 20-membered heteroaryl, 5- to 20-membered heteroaryloxy, $H[(CH_2)_nO]_m$—, —$NR_dR_e$, —$CONR_dR_e$ or —$C(O)Y_1R_d$, each of which is unsubstituted or optionally substituted with one or more $R_a$;

$R_3$ is selected from the group consisting of $C_{3-20}$ cycloalkyl, 3- to 20-membered heterocyclyl, $C_{6-20}$ aryl and 5- to 20-membered heteroaryl, each of which is unsubstituted or optionally substituted with one or more $R_b$;

each $R_a$ is the same as or different from any other one and is independently selected from the group consisting of $C_{1-40}$ alkyl, $C_{1-40}$ alkoxy, $C_{2-40}$ alkenyl, $C_{2-40}$ alkynyl, $C_{3-20}$ cycloalkyl, —F, —Cl, —Br, —I, —OH, —NH, —SH, —CN, =O or —COOH;

(i) each $R_b$ is the same as or different from any other one and is independently selected from the group consisting of —F, —Cl, —Br, —I, —SH, —OH, —CN, —COOH and the following group of $C_{1-40}$ alkyl, $C_{1-40}$ alkoxy, $C_{2-40}$ alkenyl, $C_{2-40}$ alkynyl, $C_{3-20}$ cycloalkyl, 3- to 20-membered heterocyclyl, $C_{6-20}$ aryl, 5- to 20-membered heteroaryl, $C_{3-20}$ cycloalkoxy, 3- to 20-membered heterocycloxy, $C_{6-20}$ aryloxy, 5- to 20-membered heteroaryloxy, $(C_{3-20})$cycloalkyl$(C_{1-40})$alkyl, (3- to 20-membered)heterocyclyl$(C_{1-40})$alkyl, $(C_{6-20})$aryl$(C_{1-40})$alkyl, (5- to 20-membered)heteroaryl$(C_{1-40})$alkyl, $H[(CH_2)_nO]_n$—, —$NR_cR_d$, —$C(O)NR_cR_d$, —$Y_1C(O)R_e$ and —$C(O)Y_1R_e$, each of which is unsubstituted or optionally substituted with one or more $R_a$, or, (ii) when $R_3$ is substituted with two or more identical or different $R_b$, two of which losing their hydrogen atoms or other groups respectively, are taken together with the carbon atoms to which they are attached to form a ring system $R_s$ fused with $R_3$, wherein $R_s$ is selected from the group consisting of $C_{3-20}$ cycloalkyl, 3- to 20-membered heterocyclyl, $C_{6-20}$ aryl, or 5- to 20-membered heteroaryl fused with $R_3$;

$R_c$, $R_d$ and $R_e$ are the same or different, each of which is independently selected from the group consisting of H and the following group of $C_{1-40}$ alkyl, $C_{2-40}$ alkenyl, $C_{2-40}$ alkynyl, $C_{3-20}$ cycloalkyl, 3- to 20-membered heterocyclyl, $C_{6-20}$ aryl, 5- to 20-membered heteroaryl or $CONH_2$, each of which is unsubstituted or optionally substituted with one or more $R_a$;

$Y_1$ is selected from the group consisting of a chemical bond, —O—, —S—, and the group of —NH—, $C_{1-40}$ alkyl, $C_{1-40}$ alkoxy, $C_{3-20}$ cycloalkyl, 3- to 20-membered heterocyclyl, $C_{6-20}$ aryl, 5- to 20-membered heteroaryl, or $(CH_2CH_2O)_j$—, each of which is unsubstituted or optionally substituted with one or more $R_a$;

m, n and j may be the same or different, each of which is independently selected from an integer equal to or more than 1;

$R_3$ is selected from the group consisting of $C_{3-8}$ cycloalkyl, 3- to 8-membered heterocyclyl, $C_{6-10}$ aryl and 5- to 6-membered heteroaryl, each of which is unsubstituted or optionally substituted with one or more $R_b$;

each $R_b$ is the same as or different from any other one and is independently selected from the group consisting of —F, —Cl, —Br, —I, —SH, —OH, —CN, —COOH and the following group of $C_{1-6}$ alkyl, $C_{1-6}$ alkoxy, $C_{3-8}$ cycloalkyl, 3- to 8-membered heterocyclyl, $C_{6-10}$ aryl, 5- to 6-membered heteroaryl, $C_{3-8}$ cycloalkoxy, 3- to 8-membered heterocycloxy, $C_{6-10}$ aryloxy, 5- to 6-membered heteroaryloxy, $(C_{3-8})$cycloalkyl$(C_{1-6})$alkyl, (3- to 8-membered)heterocyclyl$(C_{1-6})$alkyl, $(C_{6-10})$aryl$(C_{1-6})$alkyl, (5- to 6-membered)heteroaryl$(C_{1-6})$alkyl, $H[(CH_2)_nO]_n$—, —$NR_cR_d$, —$C(O)NR_cR_d$, —$Y_1C(O)R_e$ or —$C(O)Y_1R_e$, each of which is unsubstituted or optionally substituted with one or more $R_a$;

or, when $R_3$ is substituted with two or more identical or different $R_b$, two of which losing their hydrogen atoms or other groups respectively, are taken together with the carbon atoms to which they are attached to form a ring system $R_s$ fused with $R_3$, wherein $R_s$ is selected from the group consisting of $C_{3-8}$ cycloalkyl, 3- to 8-membered heterocyclyl, $C_{6-10}$ aryl, or 5- to 6-membered heteroaryl fused with $R_3$.

2. The amino alcohol derivative, or a pharmaceutically acceptable salt, stereoisomer, isotopic label, solvate, polymorph, or prodrug thereof according to claim 1, wherein $R_3$ is selected from the group consisting of phenyl, pyridinyl, pyrazinyl, cyclohexyl, piperidinyl and piperazinyl.

3. The amino alcohol derivative, or a pharmaceutically acceptable salt, stereoisomer, isotopic label, solvate, polymorph, or prodrug thereof according to claim 1, wherein the compound of Formula I' is selected from the group consisting of the following compounds:

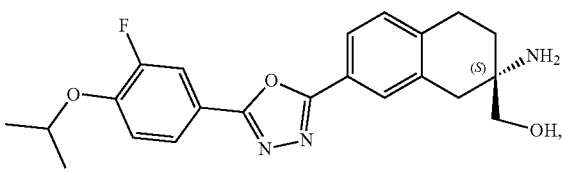

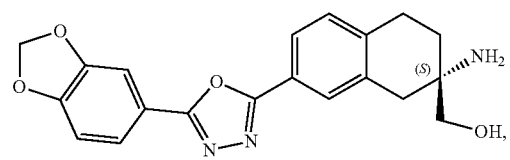

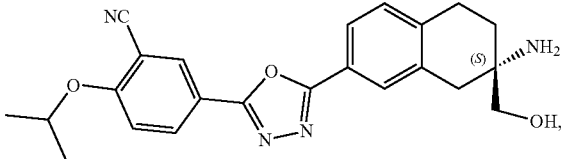

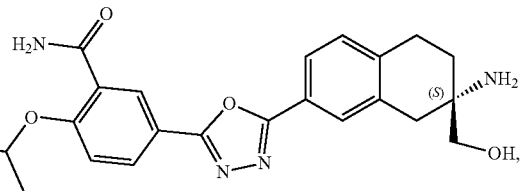

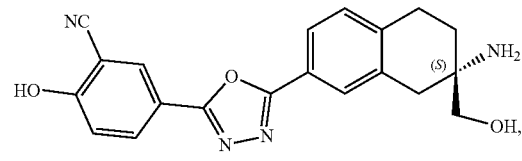

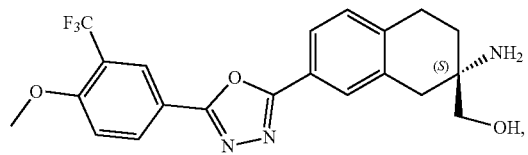

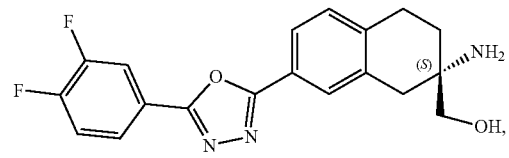

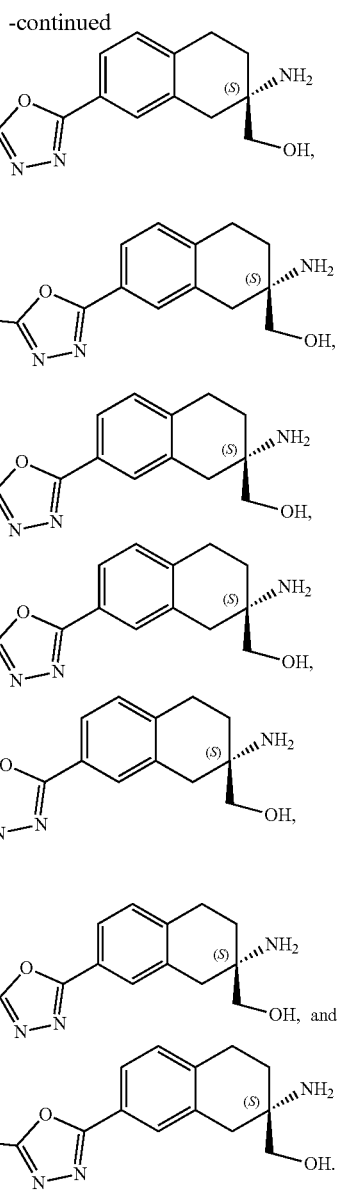

4. The amino alcohol derivative, or a pharmaceutically acceptable salt, stereoisomer, isotopic label, solvate, polymorph, or prodrug thereof according to claim 1, wherein $R_1$ and $R_2$ are the same or different, each of which is independently selected from the group consisting of H, —F, —Cl, —Br, —I, —OH, —SH, —CN, —COOH, and $C_{1-40}$ alkyl.

5. The amino alcohol derivative, or a pharmaceutically acceptable salt, stereoisomer, isotopic label, solvate, polymorph, or prodrug thereof according to claim 1, wherein $R_3$ is selected from the group consisting of phenyl, pyridin-1-yl, pyridin-2-yl, pyridin-3-yl, pyridin-4-yl, piperidin-1-yl, piperidin-2-yl, piperidin-3-yl, and piperidin-4-yl.

6. The amino alcohol derivative, or a pharmaceutically acceptable salt, stereoisomer, isotopic label, solvate, polymorph, or prodrug thereof according to claim 1, wherein each $R_b$ is the same as or different from any other one and is independently selected from the group consisting of —F, —Cl, —Br, —I, —SH, —OH, —CN, —COOH and the following group of $C_{1-6}$ alkyl (such as methyl, ethyl, propyl, isopropyl, t-butyl), alkoxy (methoxy, ethoxy, propoxy, i-propoxy, t-butoxy), C3-6 cycloalkyl, $C_{3-6}$ cycloalkoxy, alkylcarbonylamino, $C_{1-6}$ alkoxycarbonal, $C_{1-6}$ alkylcarbonyloxy, (3- to 6-membered)heterocyclyl($C_{1-6}$)alkyl, —CONH$_2$, and —NHCOCH$_3$, each of which is unsubstituted or optionally substituted with one or more $R_a$.

7. The amino alcohol derivative, or a pharmaceutically acceptable salt, stereoisomer, isotopic label, solvate, polymorph, or prodrug thereof according to claim 1, wherein each $R_b$ is the same as or different from any other one and is independently selected from the group consisting of —F, —OH, —CN, —CF$_3$, —COOH, —CONH$_2$, methoxy, ethoxy, propoxy, i-propoxy, —NHCOCH$_3$, cyclopentyl, —C(O)OCH$_3$, 1-azetidinylmethyl, 1-pyrrolidinylmethyl, and 1-piperidinylmethyl.

8. The amino alcohol derivative, or a pharmaceutically acceptable salt, stereoisomer, isotopic label, solvate, polymorph, or prodrug thereof according to claim 1, wherein when $R_3$ is substituted with two or more identical or different $R_b$, two of which losing their hydrogen atoms or other groups respectively, are taken together with the carbon atoms to which they are attached to form a ring system $R_s$ fused with $R_3$, wherein $R_s$ is a dioxol ring system fused with $R_3$.

9. The amino alcohol derivative, or a pharmaceutically acceptable salt, stereoisomer, isotopic label, solvate, polymorph, or prodrug thereof according to claim 1, wherein when $R_3$ is phenyl, which is optionally substituted with $R_{b3}$ at least in position 3 and $R_{b3}$ is an electron withdrawing group.

10. The amino alcohol derivative, or a pharmaceutically acceptable salt, stereoisomer, isotopic label, solvate, polymorph, or prodrug thereof according to claim 1, wherein when $R_3$ is phenyl, which is optionally substituted with $R_{b4}$ at least in position 4 and $R_{b4}$ is an electron donating group.

11. The amino alcohol derivative, or a pharmaceutically acceptable salt, stereoisomer, isotopic label, solvate, polymorph, or prodrug thereof according to claim 1, wherein $R_{b3}$ is selected from the group consisting of —Cl, —Br, —I, —SH, —OH, —CN, —COOH, —CONH$_2$, —CO—($C_{1-6}$) alkyl, —CO—($C_{3-6}$)cycloalkyl, and —CF$_3$; or $R_{b4}$ is selected from the group consisting of $C_{1-6}$ alkyl optionally including methyl, ethyl, propyl, isopropyl, t-butyl, $C_{1-6}$ alkoxy optionally including methoxy, ethoxy, propoxy, i-propoxy, t-butoxy, $C_{3-6}$ cycloalkyl, $C_{3-6}$ cycloalkoxy, and $C_{1-6}$ alkylcarbonylamino.

* * * * *